US011040979B2

(12) United States Patent
Hodous et al.

(10) Patent No.: US 11,040,979 B2
(45) Date of Patent: Jun. 22, 2021

(54) SUBSTITUTED PYRROLO[1,2-B]PYRIDAZINES FOR TREATING DISORDERS RELATED TO KIT AND PDGFR

(71) Applicant: Blueprint Medicines Corporation, Cambridge, MA (US)

(72) Inventors: Brian L. Hodous, Arlington, MA (US); Joseph L. Kim, Wayland, MA (US); Kevin J. Wilson, Boston, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 16/498,762

(22) PCT Filed: Mar. 29, 2018

(86) PCT No.: PCT/US2018/025193
§ 371 (c)(1),
(2) Date: Sep. 27, 2019

(87) PCT Pub. No.: WO2018/183712
PCT Pub. Date: Oct. 4, 2018

(65) Prior Publication Data

US 2020/0024280 A1 Jan. 23, 2020

Related U.S. Application Data

(60) Provisional application No. 62/479,984, filed on Mar. 31, 2017.

(51) Int. Cl.
*A61K 31/5025* (2006.01)
*C07D 487/04* (2006.01)

(52) U.S. Cl.
CPC .................................. *C07D 487/04* (2013.01)

(58) Field of Classification Search
CPC .......................... A61K 31/5025; C07D 487/04
USPC .......................................... 514/248; 544/235
See application file for complete search history.

(56) References Cited

U.S. PATENT DOCUMENTS

| | | | |
|---|---|---|---|
| 6,982,265 | B1 | 1/2006 | Hunt et al. |
| 8,609,672 | B2 | 12/2013 | Russu et al. |
| 8,802,697 | B2 | 8/2014 | Bifulco, Jr. et al. |
| 9,126,951 | B2 | 9/2015 | Bifulco, Jr. et al. |
| 9,200,002 | B2 | 12/2015 | Hodous et al. |
| 9,334,263 | B2 | 5/2016 | Hodous et al. |
| 9,340,514 | B2 | 5/2016 | Bifulco, Jr. et al. |
| 9,434,700 | B2 | 9/2016 | Bifulco, Jr. et al. |
| 9,499,522 | B2 | 11/2016 | DiPietro et al. |
| 9,688,680 | B2 | 6/2017 | Hodous |
| 9,695,165 | B2 | 7/2017 | Bifulco, Jr. et al. |
| 9,884,861 | B2 | 2/2018 | Hodous et al. |
| 9,944,651 | B2 | 4/2018 | Hodous et al. |
| 9,994,552 | B2 | 6/2018 | DiPietro et al. |
| 9,994,575 | B2 | 6/2018 | Hodous et al. |
| 10,000,490 | B2 | 6/2018 | Bifulco, Jr. et al. |
| 10,000,496 | B2 | 6/2018 | Hodous et al. |
| 10,017,512 | B2 | 7/2018 | Wenglowsky et al. |
| 10,030,005 | B2 | 7/2018 | Brubaker et al. |
| 10,035,789 | B2 | 7/2018 | Brubaker et al. |
| 10,202,365 | B2 | 2/2019 | Brooijmans et al. |
| 10,227,329 | B2 | 3/2019 | Brubaker et al. |
| 2006/0211695 | A1 | 9/2006 | Borzilleri et al. |
| 2014/0187559 | A1 | 7/2014 | Miduturu |
| 2016/0031892 | A1 | 2/2016 | Hodous |
| 2016/0102097 | A1 | 4/2016 | Hodous et al. |
| 2017/0022206 | A1 | 1/2017 | Hodous et al. |
| 2017/0029409 | A1 | 2/2017 | DiPietro et al. |
| 2017/0057953 | A1 | 3/2017 | Hodous et al. |
| 2017/0066773 | A1 | 3/2017 | Wenglowsky et al. |
| 2017/0066812 | A1 | 3/2017 | Bifulco, Jr. et al. |
| 2017/0121312 | A1 | 5/2017 | Brubaker et al. |
| 2017/0145018 | A1 | 5/2017 | Wenglowsky et al. |
| 2017/0174652 | A1 | 6/2017 | Bifulco, Jr. et al. |
| 2017/0204104 | A1 | 7/2017 | Hodous et al. |
| 2017/0253593 | A1 | 9/2017 | Bifulco, Jr. et al. |
| 2017/0267661 | A1 | 9/2017 | Kim et al. |
| 2017/0298069 | A1 | 10/2017 | Brooijmans et al. |
| 2018/0022731 | A1 | 1/2018 | Brooijmans et al. |
| 2018/0022732 | A1 | 1/2018 | Brubaker et al. |
| 2018/0362613 | A1 | 12/2018 | Bifulco, Jr. et al. |
| 2019/0119280 | A1 | 4/2019 | Hodous et al. |
| 2019/0144454 | A1 | 5/2019 | Hodous et al. |

FOREIGN PATENT DOCUMENTS

| | | | |
|---|---|---|---|
| CN | 108191874 | A | 6/2018 |
| JP | 2005503372 | A | 2/2005 |
| JP | 2006519205 | A | 8/2006 |
| JP | 2007535558 | A | 12/2007 |
| JP | 2008504366 | A | 2/2008 |
| JP | 2009514882 | A | 4/2009 |
| JP | 2009542814 | A | 12/2009 |
| RU | 2331640 | C2 | 8/2008 |

(Continued)

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Hackam, et al. JAMA, 296(14), 2006, 1731-1732.*
International Search Report and Written Opinion for Application No. PCT/US2018/025193, dated May 30, 2018, 10 pages.
Antonescu, What lessons can be learned from the GIST paradigm that can be applied to other kinase-driven cancers. J Pathol. Jan. 2011;223(2):251-261.
Bennett et al., Cecil Textbook of Medicine, 20th Edition, vol. 1, W.B. Saunders Company, Philadelphia. pp. 1004-1010, (1996).
Cairoli et al., Prognostic impact of c-KIT mutations in core binding factor leukemias: an Italian retrospective study. Blood. May 1, 2006;107(9):3463-8.

(Continued)

*Primary Examiner* — Douglas M Willis
(74) *Attorney, Agent, or Firm* — McCarter & English, LLP; Steven G. Davis; Wei Song

(57) ABSTRACT

Compounds and compositions useful for treating disorders related to KIT and PDGFR are described herein.

9 Claims, No Drawings

(56) References Cited

FOREIGN PATENT DOCUMENTS

| | | | |
|---|---|---|---|
| WO | 2000/71129 | A1 | 11/2000 |
| WO | 2001/25220 | A1 | 4/2001 |
| WO | 2003/010158 | A1 | 2/2003 |
| WO | 2003/090912 | A1 | 11/2003 |
| WO | 2004/071460 | A2 | 8/2004 |
| WO | 2004/076450 | A1 | 9/2004 |
| WO | 2005/117909 | A2 | 12/2005 |
| WO | 2006/004636 | A2 | 1/2006 |
| WO | 2006/028524 | A2 | 3/2006 |
| WO | 2007/056170 | A2 | 5/2007 |
| WO | 2007/065100 | A1 | 6/2007 |
| WO | 2007/085188 | A1 | 8/2007 |
| WO | 2008/005956 | A2 | 1/2008 |
| WO | 2009/015254 | A1 | 1/2009 |
| WO | 2009/117157 | A1 | 9/2009 |
| WO | 2010/022055 | A2 | 2/2010 |
| WO | 2010/144345 | A1 | 12/2010 |
| WO | 2011/005119 | A1 | 1/2011 |
| WO | 2011/103196 | A1 | 8/2011 |
| WO | 2012/027495 | A1 | 3/2012 |
| WO | 2014/039714 | A2 | 3/2014 |
| WO | 2014/100620 | A2 | 6/2014 |
| WO | 2014/160521 | A1 | 10/2014 |
| WO | 2015/057873 | A1 | 4/2015 |
| WO | 2015/058129 | A1 | 4/2015 |
| WO | 2016/022569 | A1 | 2/2016 |
| WO | 2017/019442 | A1 | 2/2017 |
| WO | 2018/049233 | A1 | 3/2018 |
| WO | 2018/183712 | A1 | 10/2018 |
| WO | WO 18/183712 | * | 10/2018 |
| WO | 2019/034128 | A1 | 2/2019 |

OTHER PUBLICATIONS

Cohen, The development and therapeutic potential of protein kinase inhibitors. Curr Opin Chem Biol. Aug. 1999;3(4):459-65.

Dermer, Another Anniversary for the War on Cancer. BiolTechnology. Mar. 1994;12:320.

Freshney, Culture of Animal Cells, a Manual of Basic Technique. Alan R. Liss, Inc. pp. 1-6, (1983).

Lee et al., Correlation of imatinib resistance with the mutational status of KIT and PDGFRA genes in gastrointestinal stromal tumors: a meta-analysis_ J Gastrointestin Liver Dis. Dec. 2013;22(4):413-8.

Paschka et al., Adverse prognostic significance of KIT mutations in adult acute myeloid leukemia with inv(16) and t(8;21): a Cancer and Leukemia Group B Study. J Clin Oncol. Aug. 20, 2006;24(24):3904-11.

Quintela et al., A Ready One-pot Preparation for Pyrrolo[2,1-f]-[1,2,4]triazine and Pyrazolo[5,1-c]pyrimido[4,5-e]-[1,2,4]triazine Derivatives. Tetrahedron. 1996;52(8):3037-3048.

Schnittger et al., KIT-D816 mutations in AML1-ETO-positive AML are associated with impaired event-free and overall survival. Blood. 2006;107:1791-1799.

Shallal et al., Discovery, synthesis, and investigation of the antitumor activity of novel piperazinylpyrimidine derivatives. Eur J Med Chem. Jun. 2011;46(6):2043-57.

International Search Report and Written Opinion for Application No. PCT/US2014/027008, dated Jul. 24, 2014, 11 pages.

International Search Report and Written Opinion for Application No. PCT/US2014/060746, dated Dec. 17, 2014, 8 pages.

International Search Report and Written Opinion for Application No. PCT/US2014/061211, dated Dec. 10, 2014, 9 pages.

International Search Report and Written Opinion for Application No. PCT/US2016/043301, dated Oct. 17, 2016, 10 pages.

International Search Report and Written Opinion for Application No. PCT/US2015/043624, dated Oct. 6, 2015, 7 pages.

* cited by examiner

SUBSTITUTED PYRROLO[1,2-B]PYRIDAZINES FOR TREATING DISORDERS RELATED TO KIT AND PDGFR

CROSS REFERENCE TO RELATED APPLICATIONS

This application is a U.S. national stage filing, under 35 U.S.C. § 371(c), of International Application No. PCT/US2018/025193, filed Mar. 29, 2018, which claims priority to U.S. Provisional Application No. 62/479,984, filed Mar. 31, 2017. The entire contents of each of the aforementioned applications are incorporated herein by reference.

FIELD OF THE INVENTION

This disclosure relates to compounds and compositions useful for treating disorders related to KIT and PDGFR.

BACKGROUND OF THE INVENTION

The enzyme KIT (also called CD117) is a receptor tyrosine kinase expressed on a wide variety of cell types. The KIT molecule contains a long extracellular domain, a transmembrane segment, and an intracellular portion. The ligand for KIT is stem cell factor (SCF), the binding of which to the extracellular domain of KIT induces receptor dimerization and activation of downstream signaling pathways. KIT mutations generally occur in Exons 7, 8, 9, 11, 13, 14, 17, and 18. Mutations make KIT function independent of activation by SCF, leading to a high cell division rate and possibly genomic instability. Mutant KIT has been implicated in GIST (gastrointestinal stromal tumors), e.g., exon 11 mutations are the most common. Mutant KIT has also been implicated in the pathogenesis of several other disorders and conditions including systemic mastocytosis, AML (acute myeloid leukemia), melanoma, and seminoma. In systemic mastocytosis, exon 17 mutations are most common; in melanoma, exon 13 mutations are more common. As such, there is a need for therapeutic agents that inhibit KIT, and especially agents that inhibit mutant KIT.

Platelet-derived growth factor receptors (PDGFR) are cell surface tyrosine kinase receptors for members of the platelet-derived growth factor (PDGF) family. PDGFRα and PDGFRβ are important factors regulating cell proliferation, cellular differentiation, cell growth, development, and many diseases including cancer. A PDGFRα D842V mutation has been found in a distinct subset of GIST, typically from the stomach. The D842V mutation is known to be associated with tyrosine kinase inhibitor resistance. As such, there is a need for agents that target this mutation.

DETAILED DESCRIPTION OF THE INVENTION

Definitions

"Aliphatic group" means a straight-chain, branched-chain, or cyclic hydrocarbon group and includes saturated and unsaturated groups, such as an alkyl group, an alkenyl group, and an alkynyl group.

"Alkylene" refers to a divalent radical of an alkyl group, e.g., $—CH_2—$, $—CH_2CH_2—$, and $—CH_2CH_2CH_2—$.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy, and the like.

"Alkyl" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Alkynylene" refers to a divalent radical of an alkynyl group.

"Hydroxyalkylene" or "hydroxyalkyl" refers to an alkylene or alkyl moiety in which an alkylene or alkyl hydrogen atom is replaced by a hydroxyl group. Hydroxyalkylene or hydroxyalkyl includes groups in which more than one hydrogen atom has been replaced by a hydroxyl group.

"Aromatic ring system" is art-recognized and refers to a monocyclic, bicyclic, or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Arylene" refers to a divalent aryl, wherein "aryl" is as defined herein.

"Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Aryloxy" refers to —O-(aryl), wherein the heteroaryl moiety is as defined herein.

"Halo" refers to a radical of any halogen, e.g., —F, —Cl, —Br, or —I.

"Haloalkyl" and "haloalkoxy" refer to alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Haloalkylene" refers to a divalent haloalkyl, wherein "haloalkyl" is as defined herein.

"Heteroalkyl" refers to an optionally substituted alkyl, which has one or more skeletal chain atoms chosen from an atom other than carbon, e.g., oxygen, nitrogen, sulfur, phosphorus, or combinations thereof. A numerical range may be given, e.g. $C_1$-$C_6$ heteroalkyl which refers to the number of carbons in the chain, which in this example includes 1 to 6 carbon atoms. For example, a $—CH_2OCH_2CH_3$ radical is referred to as a "$C_3$" heteroalkyl. Connection to the rest of the molecule may be through either a heteroatom or a carbon in the heteroalkyl chain.

"Heteroalkylene" refers to a divalent optionally substituted alkyl, which has one or more skeletal chain atoms chosen from an atom other than carbon, e.g., oxygen, nitrogen, sulfur, phosphorus or combinations thereof.

"Carbocyclic ring system" refers to a monocyclic, bicyclic, or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

"Cycloalkylalkyl" refers to a -(cycloalkyl)-alkyl radical where cycloalkyl and alkyl are as disclosed herein. The "cycloalkylalkyl" is bonded to the parent molecular structure through the cycloalkyl group.

"Heteroaromatic ring system" is art-recognized and refers to monocyclic, bicyclic, or polycyclic ring system, wherein at least one ring is both aromatic and comprises at least one heteroatom (e.g., N, O, or S); and wherein no other rings are heterocyclyl (as defined below). In some embodiments, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where: (i) each ring comprises a heteroatom and is aromatic, e.g., imidazolyl, oxazolyl, isoxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heteroarylene" refers to a divalent heteroaryl, wherein "heteroaryl" is as defined herein.

"Heterocyclic ring system" refers to monocyclic, bicyclic, and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which: (i) every ring is non-aromatic and at least one ring comprises a heteroatom, e.g., tetrahydrofuranyl, tetrahydropyranyl, oxetanyl, azetidinyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In some embodiments, heterocyclyl can include:

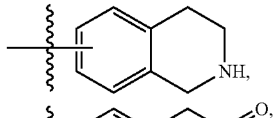

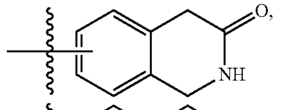

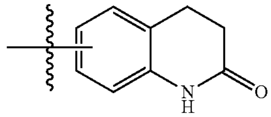

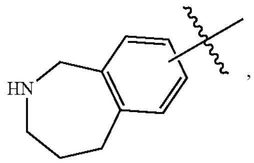

,

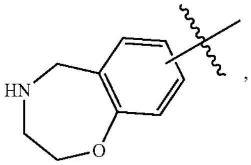

,

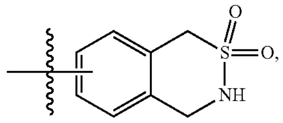

and

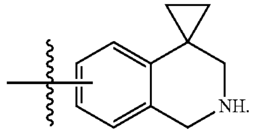

"Heterocyclylalkyl" refers to an alkyl group substituted with a heterocycle group.

"Cyano" refers to a —CN radical.

"Nitro" refers to —$NO_2$.

"Hydroxy" or "hydroxyl" refers to —OH.

"Hydroxyalkylene" refers to a divalent alkyl, e.g., —$CH_2$—, —$CH_2CH_2$—, and —$CH_2CH_2CH_2$—, in which one or more hydrogen atoms are replaced by a hydroxy, and includes alkyl moieties in which all hydrogens have been replaced by hydroxy.

"Substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position. Combinations of substituents envisioned under this disclosure include those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

Certain compounds of the disclosure may exist in particular geometric or stereoisomeric forms. The disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

If, for instance, a particular enantiomer of compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2H$), tritium ($^3H$), carbon-13 ($^{13}C$), or carbon-14 ($^{14}C$). All isotopic variations of the compounds disclosed herein, whether radioactive or not, are intended to be encompassed within the scope of the present disclosure. In addition, all tautomeric forms of the compounds described herein are intended to be within the scope of the disclosure.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

Certain compounds disclosed herein can exist in unsolvated forms as well as solvated forms, including hydrated forms. The term "hydrate" or "hydrated," as used herein, refers to a compound formed by the union of water with the parent compound.

In general, the solvated forms are equivalent to unsolvated forms and are encompassed within the scope of the present disclosure. Certain compounds disclosed herein may exist in multiple crystalline or amorphous forms. In general, all physical forms are equivalent for the uses contemplated by the present disclosure and are intended to be within the scope of the present disclosure.

As used herein, "subject," "individual," and "host" refer to either a human or a non-human animal suffering from or suspected of suffering from a disease or disorder associated with aberrant KIT expression (i.e., increased KIT activity caused by signaling through KIT) or biological activity. Such organisms include, but are not limited to, mammals (e.g., murines, simians, equines, bovines, porcines, canines, felines, and the like). In some embodiments, the subject, individual, or host is a human.

"Treat" and "treating" a disease or disorder refers to ameliorating at least one symptom of the disease or disorder. These terms, when used in connection with a condition such as a cancer, refer to one or more of: impeding growth of the cancer, causing the cancer to shrink by weight or volume, extending the expected survival time of the subject, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

The term "preventing," when used in relation to a condition or disease such as cancer, refers to a reduction in the frequency of, or delay in the onset of, symptoms of the condition or disease. Thus, prevention of cancer includes, for example, reducing the number of detectable cancerous growths in a population of subjects receiving a prophylactic treatment relative to an untreated control population, and/or delaying the appearance of detectable cancerous growths in a treated population versus an untreated control population, e.g., by a statistically and/or clinically significant amount.

The term "therapeutic effect" refers to a beneficial local or systemic effect in animals, such as mammals, for example humans, caused by administration of a compound or composition of the disclosure. The phrase "therapeutically effective amount" means that amount of a compound or composition of the disclosure that is effective to treat a disease or condition caused by over expression of KIT or aberrant KIT biological activity at a reasonable benefit/risk ratio. The therapeutically effective amount of such substance will vary depending upon the subject and disease condition being treated, the weight and age of the subject, the severity of the disease condition, the manner of administration and the like, which can readily be determined by one of skill in the art.

As used herein, "developing resistance" means that when a drug is first administered to the subject, the subject's symptoms improve, whether measured by decrease in tumor volume, a decrease in the number of new lesions, or some other means that a physician uses to judge disease progression; however, those symptoms stop improving, or even worsen at some point. At that time, the subject is said to have developed resistance to the drug.

The disclosure provides a compound of Formula (I) or a pharmaceutically acceptable salt thereof, wherein:

(I)

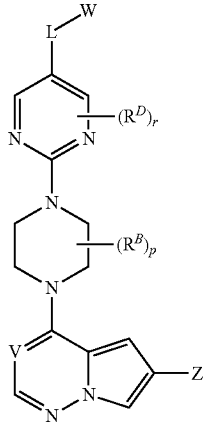

W is hydrogen or

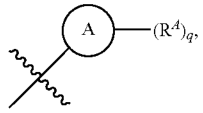

wherein ring A is chosen from aryl and heteroaryl;

V is $CR^1$;

Z is chosen from cycloalkyl, aryl, heteroaryl, and heterocyclyl, wherein each of cycloalkyl, aryl, heteroaryl, and heterocyclyl is independently substituted with 0-5 occurrences of $R^C$;

L is chosen from a bond, —($C_1$-$C_6$ alkylene)-, —($C_2$-$C_6$ alkenylene)-, —($C_2$-$C_6$ alkynylene)-, —($C_1$-$C_6$ haloalkylene)-, —($C_1$-$C_6$ heteroalkylene)-, —($C_1$-$C_6$ hydroxyalkylene)-, —C(O)—, —O—, —S—, —S(O), —$S(O)_2$—, —N($R^3$)—, —O—($C_1$-$C_6$ alkylene)-*, —($C_1$-$C_6$ alkylene)-O—*, —N($R^3$)—C(O)—*, —C(O)—N($R^3$)—*, —($C_1$-$C_6$ alkylene)-N($R^3$)—*, —N($R^3$)—($C_1$-$C_6$ alkylene)-*, —N($R^3$)—C(O)—($C_1$-$C_6$ alkylene)-*, —C(O)—N($R^3$)—($C_1$-$C_6$ alkylene)-*, —N($R^3$)—$S(O)_2$—*, —$S(O)_2$—N($R^3$)—*, —N($R^3$)—$S(O)_2$—($C_1$-$C_6$ alkylene)-*, and —$S(O)_2$—N($R^3$)—($C_1$-$C_6$ alkylene)-*, wherein each alkylene is independently substituted with 0-5 occurrences of $R^2$; and "*" represents a portion of L bound to W;

each $R^A$ is independently chosen from halo, hydroxyl, $C_1$-$C_4$ alkyl, $C_1$-$C_4$ alkenyl, $C_1$-$C_4$ alkynyl, $C_1$-$C_4$ alkoxy, $C_1$-$C_4$ haloalkyl, $C_1$-$C_4$ hydroxyalkyl, $C_1$-$C_4$ heteroalkyl, aryl, aralkyl, heteroaryl, heteroaralkyl, cycloalkyl, cycloalkylalkyl, heterocyclyl, heterocyclylalkyl, —N($R^3$)($R^3$), cyano, nitro, and —$OR^4$;

each $R^B$ is independently chosen from hydrogen, $C_1$-$C_4$ alkyl, hydroxyl, halo, $C_1$-$C_4$ alkoxy, $C_1$-$C_4$ haloalkyl, $C_1$-$C_4$ haloalkoxy, $C_1$-$C_4$ hydroxyalkyl, —N($R^3$)($R^3$), nitro, and cyano;

each $R^C$ is independently chosen from $C_1$-$C_6$ alkyl, $C_1$-$C_6$ alkenyl, $C_1$-$C_6$ alkynyl, halo, $C_1$-$C_6$ heteroalkyl, $C_1$-$C_6$ haloalkyl, $C_1$-$C_6$ haloalkoxy, $C_1$-$C_6$ hydroxyalkyl, cycloalkyl, aryl, aryloxy, aralkyl, heterocyclyl, heterocyclylalkyl, nitro, cyano, —C(O)$R^5$, —OC(O)$R^5$, —C(O)O$R^5$, —S$R^5$, —$S(O)_2R^5$, —$S(O)_2$—N($R^3$)($R^3$), —($C_1$-$C_6$ alkylene)-$S(O)_2$—N($R^3$)($R^3$), —N($R^3$)($R^3$), —C(O)—N($R^3$)($R^3$), —N($R^3$)($R^3$)—C(O)$R^5$, —($C_1$-$C_6$ alkylene)-N($R^3$)—C(O)$R^5$, —$NR^3S(O)_2R^5$, —P(O)($R^5$)($R^5$), and —$OR^4$; wherein each of alkyl, alkynyl, alkenyl, heteroalkyl, haloalkyl, haloalkoxy, hydroxyalkyl, cycloalkyl, aryl, aryloxy, aralkyl, heterocyclyl, heterocyclylalkyl is independently substituted with 0-5 occurrences of $R^a$; or 2 $R^C$ together with the carbon atom(s) to which they are attached form a cycloalkyl or heterocyclyl ring substituted with 0-5 occurrences of $R^a$;

each $R^D$ is independently chosen from halo, $C_1$-$C_4$ alkyl, $C_3$-$C_4$cycloalkyl, hydroxyl, halo, $C_1$-$C_4$ alkoxy, $C_1$-$C_4$ haloalkyl, —N($R^3$)($R^3$), and cyano;

$R^1$ is chosen from hydrogen, $C_1$-$C_4$ alkyl, $C_3$-$C_4$ cycloalkyl, hydroxyl, halo, $C_1$-$C_4$ alkoxy, $C_1$-$C_4$ haloalkyl, —N($R^3$)($R^3$), and cyano;

each $R^2$ is independently chosen from hydroxyl, halo, thiol, $C_1$-$C_6$ alkyl, $C_1$-$C_6$ alkoxy, $C_1$-$C_6$ haloalkyl, $C_1$-$C_6$ hydroxyalkyl, $C_1$-$C_6$ thioalkyl, —$NR^3R^3$, cycloalkyl, cycloalkylalkyl, heterocyclyl, and heterocyclylalkyl, wherein each of $C_1$-$C_6$ alkyl, cycloalkyl, and heterocyclyl is independently substituted with 0-5 occurrences of $R^b$; or 2 $R^2$ together with the atom(s) to which they are attached form a cycloalkyl or heterocyclyl ring;

each $R^3$ is independently chosen from hydrogen, $C_1$-$C_6$ alkyl, —C(O)—$C_1$-$C_6$ alkyl, —C(O)—NR'R', and —C(S)—NR'R';

each $R^4$ is independently chosen from hydrogen, $C_1$-$C_4$ alkyl, $C_1$-$C_4$ heteroalkyl, $C_1$-$C_4$ haloalkyl, $C_1$-$C_4$ hydroxyalkyl, and cycloalkyl;

each $R^5$ is independently chosen from hydrogen, hydroxyl, $C_1$-$C_6$ alkyl, $C_1$-$C_6$ alkoxyl and —$NR^3R^3$;

each $R^a$ and $R^b$ is independently chosen from hydrogen, halo, cyano, hydroxyl, $C_1$-$C_6$ alkoxyl, —C(O)R', C(O)OR', $C_1$-$C_6$ alkyl, $C_1$-$C_6$ haloalkyl, $C_1$-$C_6$ heteroalkyl, $C_1$-$C_6$ hydroxyalkyl, —NR'R', and cycloalkyl, wherein alkyl, haloalkyl, heteroalkyl, hydroxyalkyl, cycloalkyl is substituted with 0-5 occurrences of R';

each R' is independently chosen from hydrogen, $C_1$-$C_6$ alkyl, cycloalkyl, cycloalkylalkyl, heterocyclyl, heterocyclylalkyl, aryl, aralkyl, heteroaryl, and heteroaralkyl;

p is 0, 1, 2, 3, or 4;

q is 0, 1, 2, 3, 4, or 5; and r is 0, 1, 2, 3, or 4.

In some embodiments, the compound is chosen from compounds of Formula (Ia) and pharmaceutically acceptable salts thereof:

(Ia)

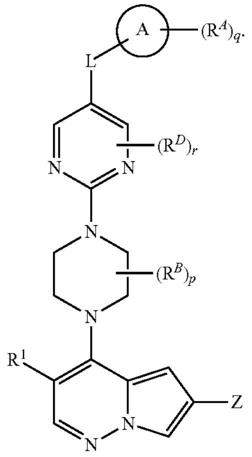

In some embodiments, the compound is chosen from compounds of Formula (II) and pharmaceutically acceptable salts thereof:

(II)

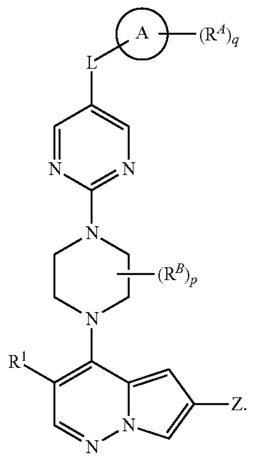

In some embodiments, the compound is chosen from compounds of Formula (IIa) and pharmaceutically acceptable salts thereof:

(IIa)

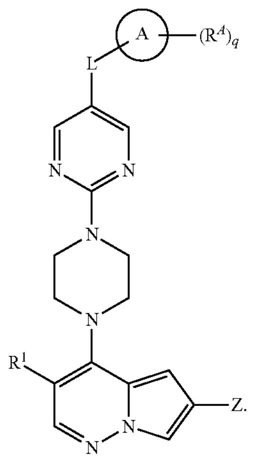

In some embodiments, the compound is chosen from compounds of Formula (III) and pharmaceutically acceptable salts thereof:

(III)

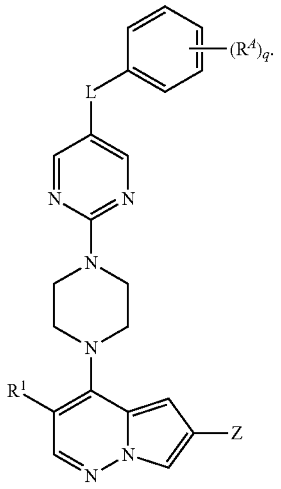

In some embodiments, the compound is chosen from compounds of Formula (IV) and pharmaceutically acceptable salts thereof:

(IV)

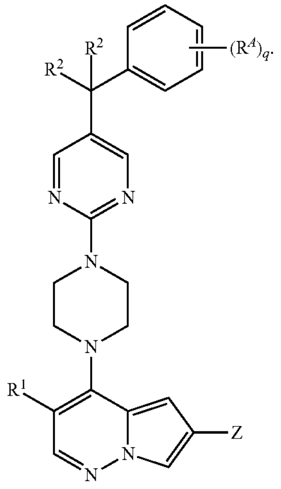

In some embodiments, the compound is chosen from compounds of Formula (Va) and Formula (Vb) and pharmaceutically acceptable salts thereof:

(Va)

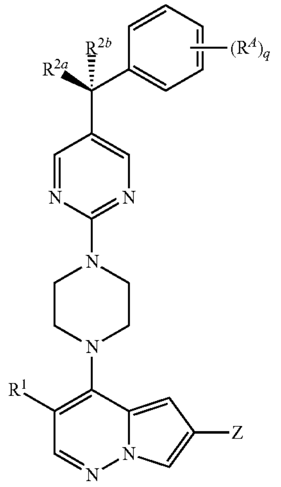

or (Vb)

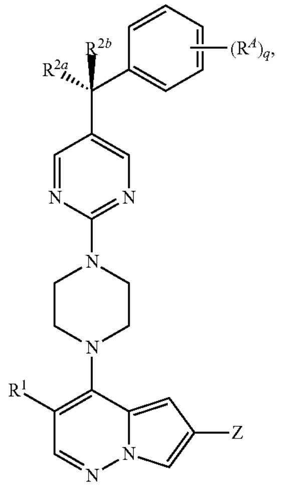

wherein $R^{2a}$ is chosen from hydroxyl, halo, thiol, $C_1$-$C_6$ alkyl, $C_1$-$C_6$ alkoxy, $C_1$-$C_6$ haloalkyl, $C_1$-$C_6$ hydroxyalkyl, $C_1$-$C_6$ thioalkyl, —$NR^3R^3$, cycloalkyl, cycloalkylalkyl, heterocyclyl, and heterocyclylalkyl, wherein each of $C_1$-$C_6$ alkyl, cycloalkyl, and heterocyclyl is independently substituted with 0-5 occurrences of $R^b$;

$R^{2b}$ is chosen from hydroxyl, halo, thiol, $C_1$-$C_6$ alkyl, $C_1$-$C_6$ alkoxy, $C_1$-$C_6$ haloalkyl, $C_1$-$C_6$ hydroxyalkyl, $C_1$-$C_6$ thioalkyl, —$NR^3R^3$, cycloalkyl, cycloalkylalkyl, heterocyclyl, and heterocyclylalkyl, wherein each of $C_1$-$C_6$ alkyl, cycloalkyl, and heterocyclyl is independently substituted with 0-5 occurrences of $R^b$;

or $R^{2a}$ and $R^{2b}$ taken together with the atom(s) to which they are attached form a cycloalkyl or heterocyclyl ring.

In some embodiments, L is —$(C(R^2)(R^2))_m$—, wherein m is 1 or 2. In some embodiments, the $R^2$ are different. In some embodiments, the $R^2$ are the same.

In some embodiments, L is

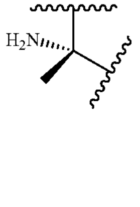

In some embodiments, $R^{2a}$ and $R^{2b}$ are different. In some embodiments, $R^{2a}$ and $R^{2b}$ are the same.

In some embodiments, each $R^2$ is independently chosen from hydrogen, $C_1$-$C_3$ alkyl, hydroxyl, $NR^3R^3$, $C_1$-$C_3$ hydroxyalkyl, $C_1$-$C_3$ haloalkyl, $C_1$-$C_3$ alkoxy, and cycloalkyl. In some embodiments, each $R^2$ is independently chosen from hydrogen, methyl, ethyl, hydroxyl, $NH_2$, $N(CH_3)_2$, $CH_2OH$, methoxy, $CH_2F$, $CHF_2$, cyclopropyl, and $CF_3$.

In some embodiments, each $R^{2a}$ and $R^{2b}$ is independently chosen from hydrogen, $C_1$-$C_3$ alkyl, hydroxyl, $NR^3R^3$, $C_1$-$C_3$ hydroxyalkyl, $C_1$-$C_3$ haloalkyl, $C_1$-$C_3$ alkoxy, and cycloalkyl.

In some embodiments, each $R^{2a}$ and $R^{2b}$ is independently chosen from hydrogen, methyl, ethyl, hydroxyl, $NH_2$, $N(CH_3)_2$, $CH_2OH$, methoxy, $CH_2F$, $CHF_2$, cyclopropyl, and $CF_3$.

In some embodiments, $R^3$ is chosen from hydrogen and $C_1$-$C_3$ alkyl.

In some embodiments, ring A is aryl, e.g., phenyl.

In some embodiments, ring A is phenyl substituted with $R^A$ is halo. In some embodiments, ring A is phenyl substituted with $R^A$ is 4-F.

In some embodiments, $R^A$ is halo. In some embodiments, $R^A$ is fluorine and chlorine.

In some embodiments, q is 0, 1, 2, or 3. In some embodiments, q is 0. In some embodiments, q is 1. In some embodiments, q is 2. In some embodiments, q is 3.

In some embodiments, Z is monocyclic or bicyclic heteroaryl. In some embodiments, Z is monocyclic heteroaryl. In some embodiments, Z is chosen from pyrazolyl, isoxazolyl, thiophenyl, thiazolyl, and pyridyl. In some embodiments, Z is a monocyclic or bicyclic aryl. In some embodiments, Z is monocyclic aryl e.g., phenyl. In some embodiments, Z is pyrazolyl. In some embodiments, Z is

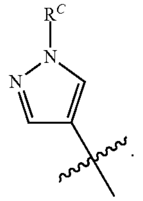

In some embodiments, each $R^C$ is chosen from $C_1$-$C_3$ alkyl and halo; or the occurrence of $R^C$ is 0. In some embodiments, $R^C$ is methyl.

In some embodiments, $R^1$ is halo, hydrogen, or CN. In some embodiments, $R^1$ is halo or hydrogen. In some embodiments, $R^1$ is halo. In some embodiments, $R^1$ is hydrogen. In some embodiments, $R_1$ is chosen from F and Cl. In some embodiments, $R^1$ is CN.

In some embodiments, $R^1$ is not $C_1$-$C_4$ alkyl, $C_3$-$C_4$ cycloalkyl, hydroxyl, $C_1$-$C_4$ alkoxy, $C_1$-$C_4$ haloalkyl, or —$N(R^3)(R^3)$.

In some embodiments, $R^B$ is chosen from halo or $C_1$-$C_3$ alkyl. In some embodiments, $R^B$ is methyl.

In some embodiments, p is 0 or 1.

In another aspect, the disclosure provides a pharmaceutical composition comprising a compound chosen from compounds of Formula (I), (II), (III), (IV), (Va), and (Vb) described herein (e.g., a compound in Table 1) and pharmaceutically acceptable salts thereof.

Table 1 below shows the structures of compounds described herein.

TABLE 1

| Compound Number | Structure |
|---|---|
| 1 | 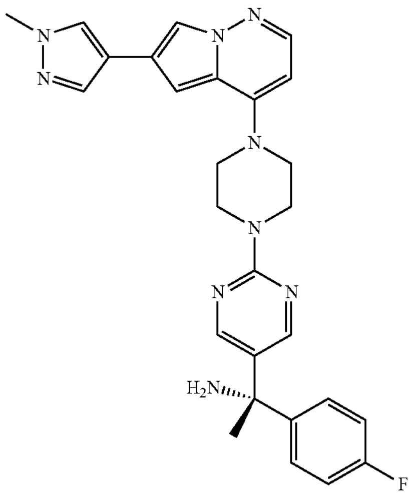 [SMILES: Cn1cc(-c2cc3c(N4CCN(c5ncc([C@@](C)(N)c6ccc(F)cc6)cn5)CC4)ccnn3c2)cn1] |
| 2 | 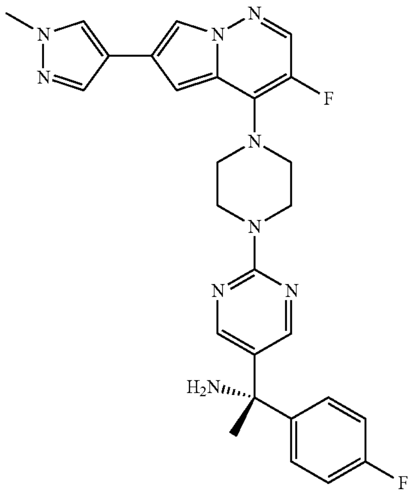 [SMILES: Cn1cc(-c2cc3c(N4CCN(c5ncc([C@@](C)(N)c6ccc(F)cc6)cn5)CC4)c(F)cnn3c2)cn1] |
| 3 | 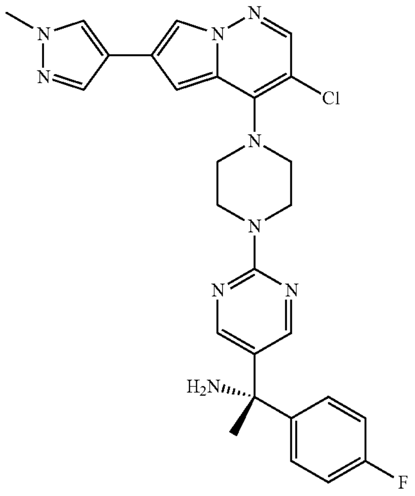 [SMILES: Cn1cc(-c2cc3c(N4CCN(c5ncc([C@@](C)(N)c6ccc(F)cc6)cn5)CC4)c(Cl)cnn3c2)cn1] |

TABLE 1-continued

| Compound Number | Structure |
|---|---|
| 4 | 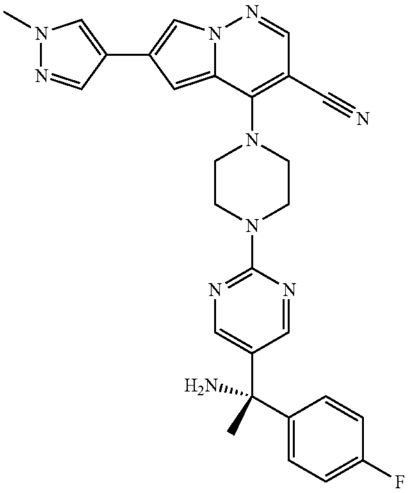 [SMILES: Cn1cc(-c2cc3c(N4CCN(c5ncc([C@@](C)(N)c6ccc(F)cc6)cn5)CC4)c(C#N)cnn3c2)cn1] |

Pharmaceutically acceptable salts of these compounds are also contemplated for the uses described herein.

"Pharmaceutically acceptable salt" refers to any salt of a compound of the disclosure which retains its biological properties and which is not toxic or otherwise undesirable for pharmaceutical use. Pharmaceutically acceptable salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo [2.2.2]-oct-2-ene-1-carboxylic, glucoheptonic, 3-phenylpropionic, trimethylacetic, tert-butyl acetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like.

The disclosure provides a method of treating a condition, e.g., a cancer, comprising administering to a subject in need thereof a therapeutically effective amount of a compound described herein (e.g., a compound of Formula (I), (II), (III), (IV), (Va) or (Vb), e.g., a compound in Table 1) or a pharmaceutically acceptable salt thereof, or a pharmaceutical composition thereof, wherein said condition is chosen from gastrointestinal stromal tumor (GIST), mastocytosis (e.g., cutaneous mastocytosis (CM) and systemic mastocytosis (SM) (e.g., indolent (ISM), smoldering (SSM), aggressive (ASM), SM with associated hemotologic non-mast cell lineage disease (SM-AHN), and mast cell leukemia (MCL)), melanoma, seminoma, intercranial germ cell tumors, mediastinal B-cell lymphoma, acute myeloid leukemia, glioblastoma, pediatric high grade glioma, DIPG, and myelodysplastic syndrome/myeloproliferative syndrome (MDS/NPN)).

In another aspect, the disclosure provides a method of treating mastocytosis comprising administering to a subject in need thereof a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof.

In another aspect, the disclosure provides a method of treating gastrointestinal stromal tumor (GIST) comprising administering to a subject a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof.

In another aspect, the disclosure provides a method of treating acute myeloid leukemia (AML) comprising administering to a subject in need thereof a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof.

In another aspect, the disclosure provides a method of treating a condition mediated by mutant KIT, wherein said KIT has a mutation in Exon 11, 13, 14, 17, or 18, the method comprising administering to a subject in need thereof a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof. In one aspect, the condition is GIST and the mutation is in Exon 11. In one aspect, the condition is SM and the mutation is in Exon 17. In one aspect, the condition is melanoma and the mutation is in Exon 13.

In another aspect, the disclosure provides a method of treating a condition mediated by mutant KIT, wherein said KIT is mutated at residue 559, 560, 670, 654, or 670, the method comprising administering to a subject in need thereof a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof. In some embodiments, said KIT is mutated in Exon 11 at residue 559 or 560. In some embodiments, the condition is GIST. In some embodiments, said KIT is mutated in Exon 13 at residue 654. In some embodiments, the condition is melanoma. In some embodiments, said KIT is mutated in Exon 14 at residue 670.

In another aspect, the disclosure provides a method of treating a condition mediated by mutant PDGFRα, the method comprising administering to a subject in need thereof a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof. In some embodiments, said PDGFRα is amplified PDGFRα. In some embodiments, the condition is glioblastoma. In some embodiments, the condition is pediatric high grade glioma or DIPG (Diffuse Intrinsic Pontine Glioma). In some embodiments, the condition is non-small cell lung cancer (NSCLC).

In another aspect, the disclosure provides a method of treating a condition mediated by mutant PDGFRα and mutant KIT, the method comprising administering to a subject in need thereof a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof. In some embodiments, PDGFRα is amplified and KIT is co-amplified. In some embodiments, the condition is non-small cell lung cancer (NSCLC).

In another aspect, the disclosure provides a method of treating a condition mediated by mutant PDGFRα, the method comprising administering to a subject in need thereof a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof. In some embodiments, the mutant PDGFRα is a gene rearrangement. In some embodiments, the condition is MDS/MPN or aggressive SM.

In another aspect, the disclosure provides a method of treating a condition mediated by mutant PDGFRα, wherein said PDGFRα has a mutation in Exon 18, the method comprising administering to a subject in need thereof a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof. In some embodiments, said PDGFRα is mutated at residue D842V. In some embodiments, the condition is GIST.

In another aspect, the disclosure provides a method of treating a condition mediated by KIT, the method comprising administering to a subject a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof.

In another aspect, the disclosure provides a method of treating a condition mediated by KIT, the method comprising administering to a subject a therapeutically effective amount of a compound described herein (e.g., a compound of Formula (I), (II), (III), (IV), (Va) or (Vb), e.g., a compound in Table 1) or a pharmaceutically acceptable salt thereof, or a pharmaceutical composition thereof, in combination with a therapeutically effective amount of a second agent, wherein the second agent is active against a mutant KIT having a mutation in Exon 9 or Exon 11.

In some embodiments, the compound and the agent are administered during the same time period. In some embodiments, the compound and the agent are not administered during the same time period.

In another aspect, the disclosure provides a method of treating a condition mediated by KIT, the method comprising administering to a subject:

(a) a therapeutically effective amount of a compound described herein (e.g., a compound of Formula (I), (II), (III), (IV), (Va), or (Vb), e.g., a compound in Table 1) or a pharmaceutically acceptable salt thereof, or a pharmaceutical composition thereof;

(b) a therapeutically effective amount of an agent active against mutant KIT A, wherein such mutant KIT A has a mutation in Exon 9 or Exon 11; and (c) a therapeutically effective amount of an agent active against a mutant KIT B, wherein such mutant KIT B has a mutation that is not in Exon 9 or 11.

In another aspect, the disclosure provides a method of treating a condition in a subject, said method comprising:

(a) determining if, having determined if, or receiving information that the subject has a mutant KIT or PDGFRα mutant cell, cancer, gene, or gene product, (b) identifying the subject as responsive to a compound of the disclosure (e.g., a compound of Formula (I), (II), (III), (IV), (Va) or (Vb), e.g., a compound in Table 1) when the subject has a mutant KIT or PDGFRα cell, cancer, gene, or gene product as disclosed herein; and (c) administering an effective amount of the compound the subject.

Methods for determining if a subject has a mutant KIT or PDGRFa include hybridization-based methods, amplification-based methods, microarray analysis, flow cytometry analysis, DNA sequencing, next-generation sequencing (NGS), primer extension, PCR, in situ hybridization, dot blot, and Southern blot.

The compounds described herein can be useful for treating conditions associated with aberrant KIT activity, in humans or non-humans. Activating mutations in KIT are found in multiple indications, including systemic mastocytosis (SM), GIST (gastrointestinal stromal tumors), AML (acute myeloid leukemia), melanoma, seminoma, intercranial germ cell tumors, and mediastinal B-cell lymphoma.

Mastocytosis refers to a group of disorders characterized by excessive mast cell accumulation in one tissue, or in multiple tissues. Mastocytosis is subdivided into two groups of disorders: (1) cutaneous mastocytosis (CM) describes forms that are limited to the skin; and (2) systemic mastocytosis (SM) describes forms in which mast cells infiltrate extracutaneous organs, with or without skin involvement. SM is further subdivided into five forms: indolent (ISM); smoldering (SSM); aggressive (ASM); SM with associated hemotologic non-mast cell lineage disease (SM-AHN); and mast cell leukemia (MCL).

Diagnosis of systemic mastocytosis is based in part on histological and cytological studies of bone marrow showing infiltration by mast cells of frequently atypical morphology, which frequently abnormally express non-mast cell markers (CD25 and/or CD2). Diagnosis of SM is confirmed when bone marrow mast cell infiltration occurs in the context of one of the following: (1) abnormal mast cell morphology (spindle-shaped cells); (2) elevated level of serum tryptase above 20 ng/mL; or (3) the presence of the activating KIT D816 mutation.

Activating mutations at the D816 position are found in the vast majority of mastocytosis cases (90-98%), with the most common mutations being D816V and D816H, and D816Y. The D816 positions found in the activation loop of the kinase domain, and mutation to V, H, or Y leads to constitutive activation of KIT kinase.

The compounds described herein may also be useful to treat GIST. Complete surgical resection remains the principal treatment of choice for subjects with a primary GIST. Surgery is effective in approximately 50% of subjects with GIST; of the remaining subjects, tumor recurrence is frequent. Primary treatment with a KIT inhibitor such as imatinib has also been shown to be sufficient for initial treatment. However, resistance to imatinib occurs within months through somatic mutation. These secondary imatinib resistant mutations are most frequently located on Exon 13, 14, 17, or 18. Sunitinib is the standard of care second line treatment for most imatinib resistant tumors and is effective for those containing mutations in Exons 11, 13, and 14. However, secondary KIT mutations in Exons 17 and 18 are resistant to sunitinib treatment and furthermore, tumors containing tertiary resistance mutations in Exon 17 and 18 emerge several months after sunitinib treatment. Regorafenib has shown promising results in a phase 3 clinical trial of imatinib, sunitinib resistant GISTs with activity against several but not all Exon 17 and 18 mutations, of which D816 is one. Thus, there is a need for therapeutic agents to treat GIST subjects with Exon 17 mutations not addressed by regorafenib.

In one aspect, the compounds disclosed herein may be useful to treat a drug-resistant cancer. In some embodiments, the cancer is resistant to imatinib. In some embodiments, the cancer is resistant to sunitinib. In some embodiments, the cancer is GIST.

In another aspect, the compounds disclosed herein may be useful to treat GIST in a subject previously treated with an anti-cancer agent chosen from imatinib, regorafenib, and Brostallicin.

In addition to the use of the compounds described herein as single agents in the refractory GIST setting, the use of combinations of imatinib, sunitinib, and/or regorafenib with the compounds disclosed herein may allow for the prevention of emergence of KIT mutations e.g., mutations in Exon 13, 14, 17 and/or 18. In one aspect, the use of the compounds described herein as single agents in the refractory GIST setting, the use of combinations of imatinib, sunitinib, and/or regorafenib with the compounds disclosed herein may allow for the prevention of emergence of Exon 17 mutations.

There is a subset of GIST subjects with a D842V mutation in PDGFRα; this subgroup of GIST subjects can be stratified by identifying this mutation. This subset of subjects is refractory to all tyrosine kinase inhibitors currently available. The compounds described herein, due to their activity against PDGFRα D842V, can be useful in treating these subjects.

The compounds described herein may also be useful in treating AML. AML subjects harbor KIT mutations as well, with the majority of these mutations at the D816 position.

In addition, mutations in KIT have been linked to Ewing's sarcoma, DLBCL (diffuse large B cell lymphoma), dysgerminoma, MDS (myelodysplastic syndrome), NKTCL (nasal NK/T-cell lymphoma), CMML (chronic myelomonocytic leukemia), and brain cancers.

The compounds disclosed herein may be used to treat conditions associated with the KIT mutations in Exon 9, Exon 11, Exon 13, Exon 14, Exon 17, and/or Exon 18. They may also be used to treat conditions associated with wild-type KIT. The compounds described herein may be used as single agents to treat the conditions described herein, or they may be used in combination with other therapeutic agents, including, without limitation, imatinib, sunitinib and regorafenib. Other agents include the compounds described in WO 2014/039714 and WO 2014/100620.

Compounds described herein can be active against one or more KIT mutations (e.g., V559D/T670I, V559D/V654A, and V560G), and much less active against wild-type KIT. The V559 and V560 mutations are in Exon 11. T670I is in Exon 14, and V654A is in Exon 13. In one aspect, compounds described herein are active against the V559D/T670I KIT mutation. This is advantageous because other known KIT inhibitors lack activity against the V559D/T670I I KIT mutation. Compounds described herein can also be active against one or more KIT mutations in Exon 17 (e.g., D816V, D816Y, D816F, D816K, D816H, D816A, D816G, D820A, D820E, D820G, N822K, N822H, Y823D, and A829P), and much less active against wild-type KIT. These compounds can be administered in combination with an agent that is (a) active against other activating mutations of KIT, such as Exon 9 and 11 mutations, but (b) not active against the Exon 17 mutations. Such agents include imatinib, sunitinib, and regorafenib. The combination of the compound and the agent will thus inhibit Exon 17 mutant KIT, as well as inhibiting Exon 9/11 mutant KIT. The compound and agent can be co-administered, or administered in an alternating regimen. That is, the Exon 17 mutant KIT inhibitor can be administered alone for a period of time; then the Exon 9/11 mutant KIT inhibitor can be administered alone for a period of time following. This cycle may then be repeated. It is believed that such a regimen could slow the development of resistance to the Exon 17 mutant KIT inhibitor and/or the Exon 9/11 mutant KIT inhibitor.

In addition, compounds described herein that can be selective for Exon 17 KIT mutations can be administered with agents that are active against Exon 9/11 mutations, in combination with a third agent that covers mutations that are missed with the two-way combo. The combination of the three agents could inhibit a spectrum of KIT mutations, as well as wild-type KIT in some instances. The agents can be administered simultaneously, or in an alternating regimen. They can be administered one at a time, or two agents can be administered together for a period of time; then the third agent can be administered alone for a following period of time. It is believed that such a regimen can slow the development of resistance to the mutant KIT inhibitors.

While it is possible for a compound disclosed herein to be administered alone, in some embodiments, a compound of the disclosure is administered as a pharmaceutical formulation, wherein the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase “pharmaceutically acceptable” is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer’s solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds disclosed herein are administered as pharmaceuticals, to humans and animals, they can be given per se or as a pharmaceutical composition containing, for example, 0.1 to 99.5% (e.g., 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

Actual dosage levels of the active ingredients in the pharmaceutical compositions of this disclosure may be varied so as to obtain an amount of the active ingredient that is effective to achieve the desired therapeutic response for a particular subject, composition, and mode of administration, without being toxic to the subject.

The selected dosage level and treatment regimen will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the subject being treated, the judgment of the treating physician, the severity of the particular disease being treating and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound that is the lowest dose effective to produce a therapeutic effect. Such an effective dose will generally depend upon the factors described above.

Synthesis

Compounds of the disclosure, including salts and N-oxides thereof, can be prepared using known organic synthesis techniques and can be synthesized according to any of numerous protocol is meant to provide general guidance in connection with preparing the compounds of the disclosure. One skilled in the art would understand that the preparations shown in the Scheme can be modified or optimized using general knowledge of organic chemistry to prepare various compounds of the disclosure.

Synthetic Protocol 1

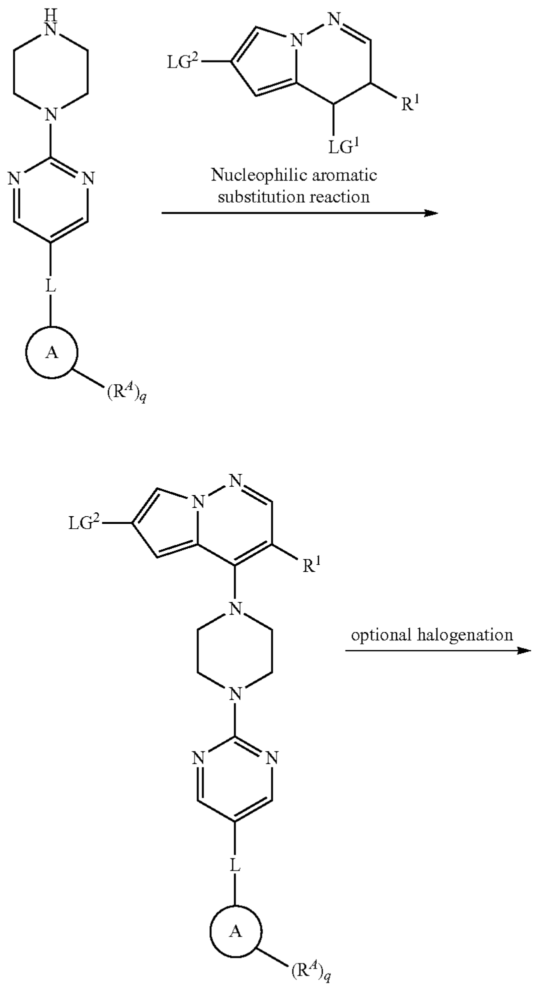

$R^1$ = H or cyano $LG^2$ = halogen (e.g., bromo or chloro)

Z-(B or Sn group)

-continued

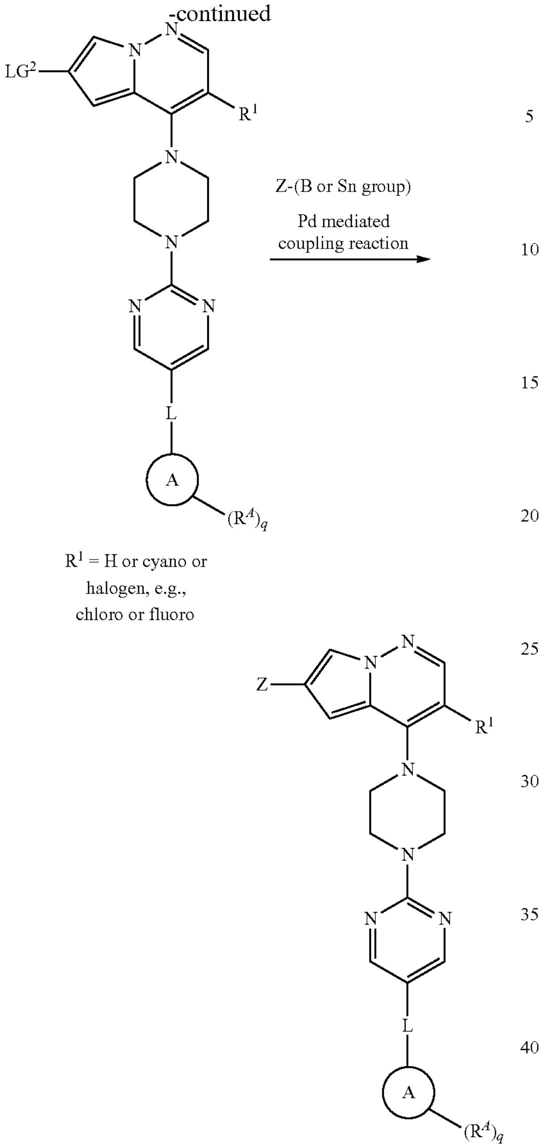

The pyrrolopyridazine can be substituted with an amine, such as a substituted piperazine, under nucleophilic aromatic substitution reaction conditions ($LG^1$ can be, e.g., chloro, —OTf (trifluoromethanesulfonate)) using an amine base such as diisopropylethylamine (DIPEA) or triethylamine (TEA) in a polar solvent such as dioxane or dimethylformamide or a non-polar solvent such as DCM to provide the piperazine-substituted pyrrolopyridazine. The piperazine-substituted pyrrolopyridazine can be coupled ($LG^2$ can be, e.g., Cl, Br, or I) to a boron, tin or zinc aryl, heteroaryl, alkenyl, or alkyl reagent via a palladium-mediated coupling reaction, e.g., Suzuki, Stille, Negishi coupling, to provide the product, for example, Compound 1. Optionally, the piperazine-substituted pyrrolopyridazine can be halogenated, prior to the palladium-mediated coupling reaction, using a halogenating agent, such as a chlorinating or fluorinating agent, which can provide the product, for example, Compounds 2 and 3. As shown below, Compounds 1, 2, 3, and 4 were prepared using Synthetic Protocol 1.

The reactions for preparing compounds of the disclosure can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC).

LC-MS: Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS: Preparative HPLC was performed on a Shimadzu Discovery VP® Preparative system fitted with a Luna 5 u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Chiral HPLC: Preparative HPLC to resolve chiral mixtures was performed on a Thar SFC Pre-80 instrument fitted with a Chiralpak AS-H column (5 mm, 3.0 cm id×25 cm L). The mobile phases consisted of SFC $CO_2$ (A) and MeOH/0.1% $NH_4OH$ (B). A constant gradient from 67% to 33% (B) was maintained at a flow rate of 65 g/min, with a system back pressure of 100 bar. The separation progress was monitored by UV detection at a wavelength of 220 nm.

Silica gel chromatography: Silica gel chromatography was performed on either a Teledyne Isco CombiFlash® Rf unit or a Biotage® Isolera Four unit.

Proton NMR: Unless otherwise indicated, all $^1H$ NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-$d_6$ solvent as parts-per million (ppm) with respect to residual DMSO (2.50 ppm).

EXAMPLES

The following examples are intended to be illustrative, and are not meant in any way to be limiting.

Example 1. Synthesis of (S)-1-(4-fluorophenyl)-1-(2-(4-(6-(1-methyl-1H-pyrazol-4-yl)pyrrolo[1,2-b]pyridazin-4-yl)piperazin-1-yl)pyrimidin-5-yl)ethanamine (Compound 1)

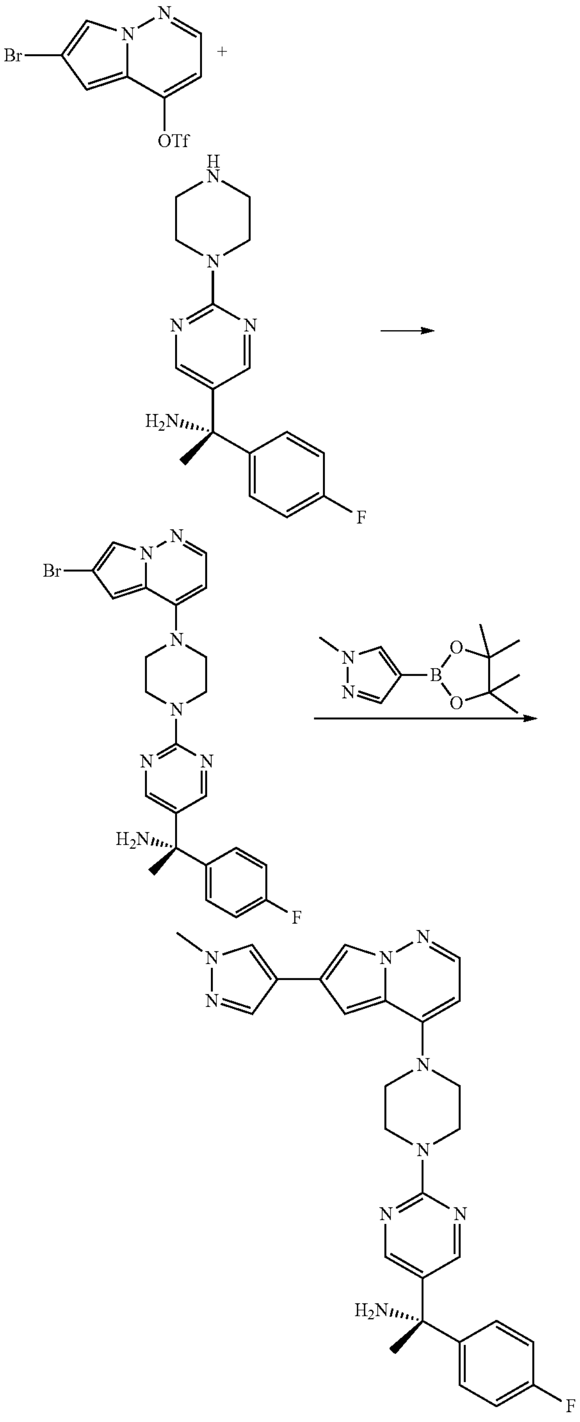

Step 1: Synthesis of (S)-1-(2-(4-(6-bromopyrrolo[1,2-b]pyridazin-4-yl)piperazin-1-yl)pyrimidin-5-yl)-1-(4-fluorophenyl)ethanamine

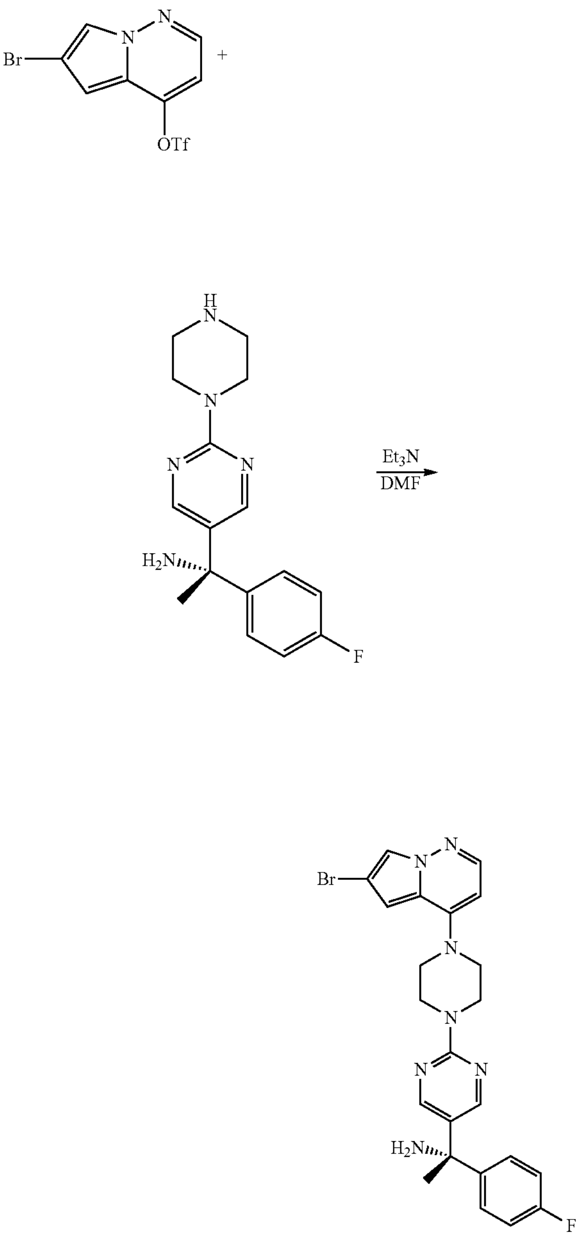

A mixture of 6-bromopyrrolo[1,2-b]pyridazin-4-yl trifluoromethanesulfonate (140 mg, 298 μmol), (S)-1-(4-fluorophenyl)-1-(2-(piperazin-1-yl)pyrimidin-5-yl)ethanamine (98.5 mg, 327 μmol), and triethylamine (60.3 mg, 596 μmol) in DMF (3 mL) was stirred at 100° C. for 16 hours. After the reaction mixture was cooled to room temperature, the mixture was extracted with ethyl acetate (EtOAc). The organic phase was dried over $Na_2SO_4$ and concentrated. The residue was purified by flash column chromatography (DCM/MeOH=10/1) to afford the title compound (140 mg, yield 72%) as a brown oil. MS (ES+) $C_{23}H_{23}BrFN_7$ requires: 495, 497, found: 496, 498 $[M+H]^+$.

Step 2: Synthesis of (S)-1-(4-fluorophenyl)-1-(2-(4-(6-(1-methyl-1H-pyrazol-4-yl)pyrrolo[1,2-b]pyridazin-4-yl)piperazin-1-yl)pyrimidin-5-yl)ethanamine

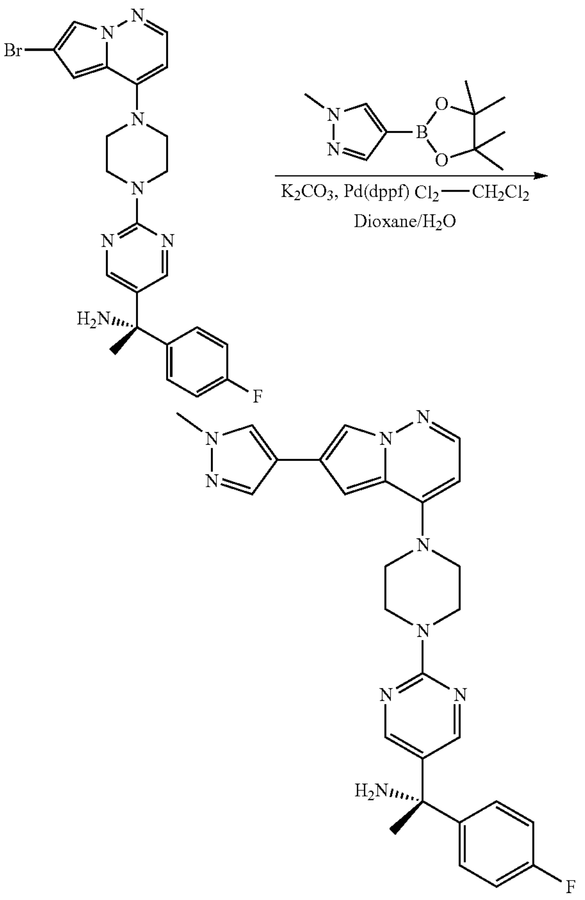

A mixture of (S)-1-(2-(4-(6-bromopyrrolo[1,2-b]pyridazin-4-yl)piperazin-1-yl)pyrimidin-5-yl)-1-(4-fluorophenyl)ethanamine (140 mg, 213 μmol), 1-methyl-4-(4,4,5,5-tetramethyl-1,3,2-dioxaborolan-2-yl)-1H-pyrazole (57.4 mg, 276 μmol), $K_2CO_3$ (58.7 mg, 426 μmol), and Pd(dppf)$Cl_2$—$CH_2Cl_2$ (17.3 mg, 21.3 μmol) in dioxane/water (2 mL/0.2 mL) was irradiated under microwave at 100° C. for 40 minutes. The solvents were removed in vacuo, and the residue was purified by Prep-HPLC to afford the title compound (41.0 mg, yield 39%) as a light yellow solid.

Example 2. Synthesis of (S)-1-(2-(4-(3-fluoro-6-(1-methyl-11H-pyrazol-4-yl)pyrrolo[1,2-b]pyridazin-4-yl)piperazin-1-yl)pyrimidin-5-yl)-1-(4-fluorophenyl)ethanamine (Compound 2)

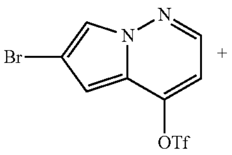

-continued

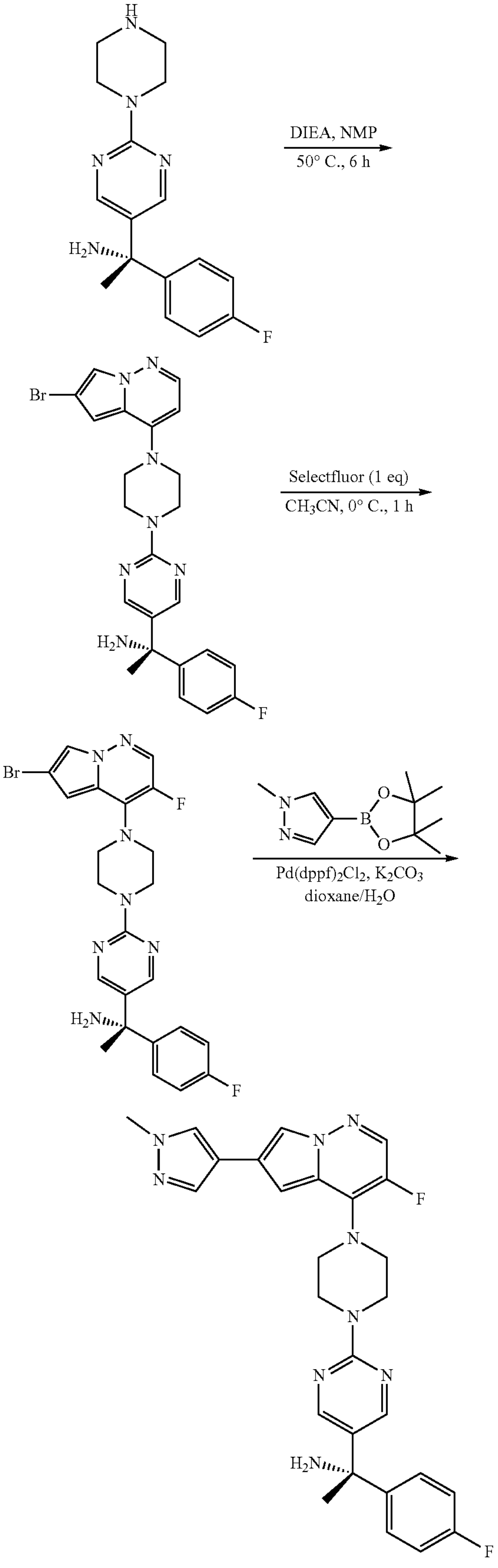

Step 1: Synthesis of (S)-1-(2-(4-(6-bromopyrrolo[1,2-b]pyridazin-4-yl)piperazin-1-yl)pyrimidin-5-yl)-1-(4-fluorophenyl)ethanamine

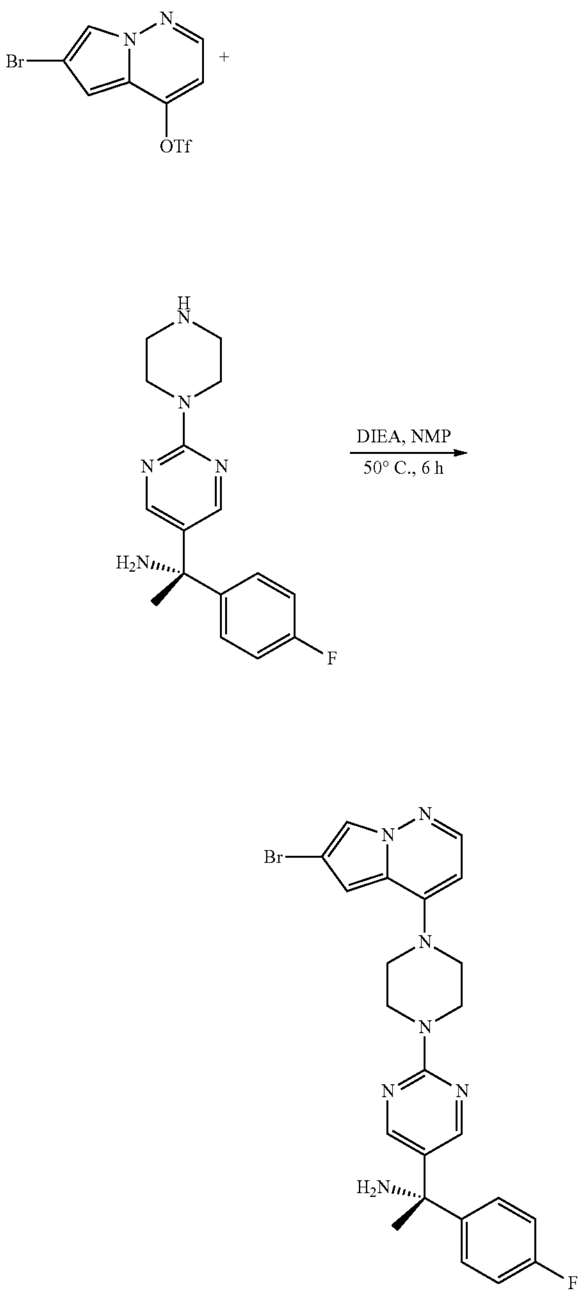

A mixture of 6-bromopyrrolo[1,2-b]pyridazin-4-yl trifluoromethanesulfonate (518 mg, 1.5 mmol), (S)-1-(4-fluorophenyl)-1-(2-(piperazin-1-yl)pyrimidin-5-yl)ethanamine (452 mg, 1.5 mmol) and DIEA (388 mg, 3 mmol) in NMP (10 mL) was stirred at 50° C. for 6 hours. The reaction mixture was cooled to room temperature and then washed with water. The organic layer was dried, concentrated and purified by silica gel column (PE/EtOAc=1:1) to give the title product (355 mg) as a yellow solid. MS (ES+) $C_{23}H_{23}BrFN_7$ requires: 495, 497, found 496, 498 $[M+H]^+$.

Step 2: Synthesis of (S)-1-(2-(4-(6-bromo-3-fluoropyrrolo[1,2-b]pyridazin-4-yl)piperazin-1-yl)pyrimidin-5-yl)-1-(4-fluorophenyl)ethanamine

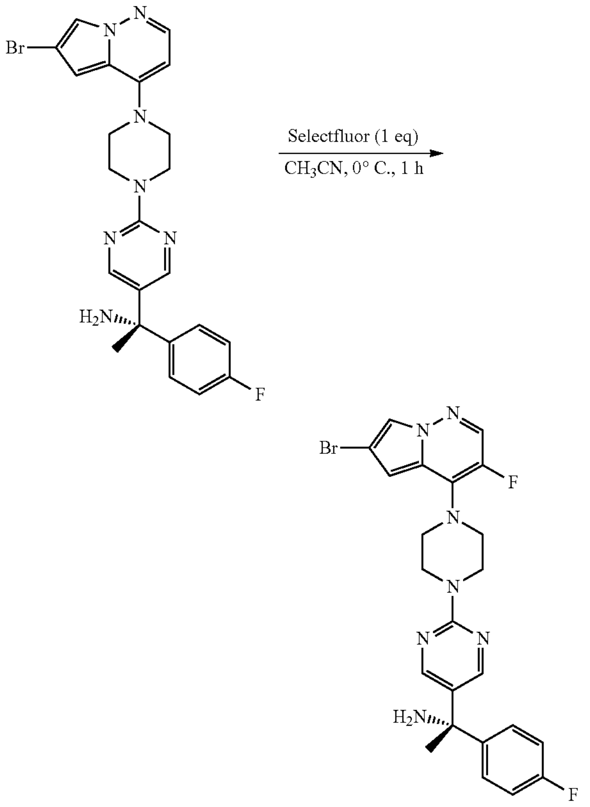

To a solution of (S)-1-(2-(4-(6-bromopyrrolo[1,2-b]pyridazin-4-yl)piperazin-1-yl)pyrimidin-5-yl)-1-(4-fluorophenyl)ethanamine (348 mg, 0.7 mmol) in acetonitrile (5 mL) was added selectfluor (249 mg, 0.7 mmol) at 0° C. The mixture was stirred at 0° C. for 1 hour. The reaction mixture was concentrated and purified by silica gel column (PE/EtOAc=1:1) to give the title product (130 mg) as a yellow solid. MS (ES+) $C_{23}H_{22}BrF_2N_7$ requires: 513, 515, found 514, 516 $[M+H]^+$.

Step 3: Synthesis of (S)-1-(2-(4-(3-fluoro-6-(1-methyl-1H-pyrazol-4-yl)pyrrolo[1,2-b]pyridazin-4-yl)piperazin-1-yl)pyrimidin-5-yl)-1-(4-fluorophenyl)ethanamine

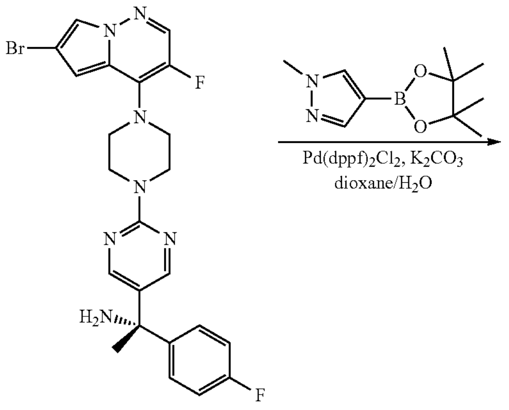

-continued

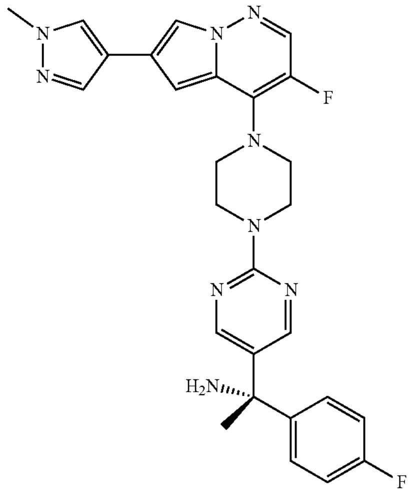 [SMILES: Cn1cc(-c2cc3c(N4CCN(c5ncc([C@@](C)(N)c6ccc(F)cc6)cn5)CC4)c(F)cnn3c2)cn1]

A mixture of (S)-1-(2-(4-(6-bromo-3-fluoropyrrolo[1,2-b]pyridazin-4-yl)piperazin-1-yl)pyrimidin-5-yl)-1-(4-fluorophenyl)ethanamine (130 mg, 0.25 mmol), 1-methyl-4-(4,4,5,5-tetramethyl-1,3,2-dioxaborolan-2-yl)-1H-pyrazole (63 mg, 0.3 mmol), $Pd(dppf)_2Cl_2$ (20 mg, 0.025 mmol) and $K_2CO_3$ (69 mg, 0.5 mmol) in dioxane/water (4 mL/1 mL) was purged with $N_2$ and stirred at 100° C. for 6 hours. The reaction mixture was cooled and filtered through Celite. The filtrate was concentrated and the crude was purified by Prep-HPLC to give the title product (52 mg) as a yellow solid.

Example 3. Synthesis of (S)-1-(2-(4-(3-chloro-6-(1-methyl-1H-pyrazol-4-yl)pyrrolo[1,2-b]pyridazin-4-yl)piperazin-1-yl)pyrimidin-5-yl)-1-(4-fluorophenyl) ethanamine (Compound 3)

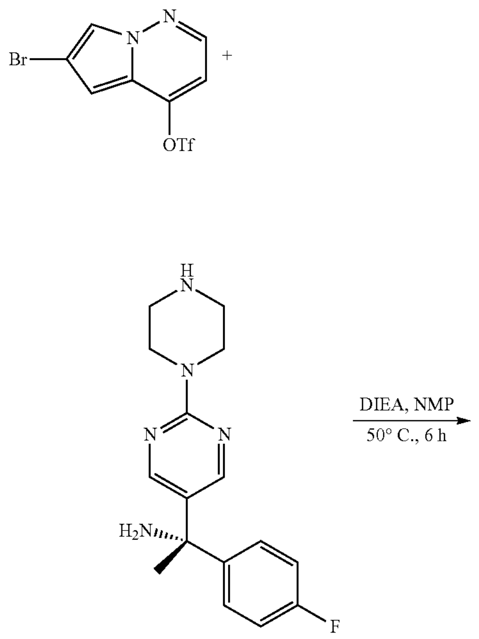

-continued

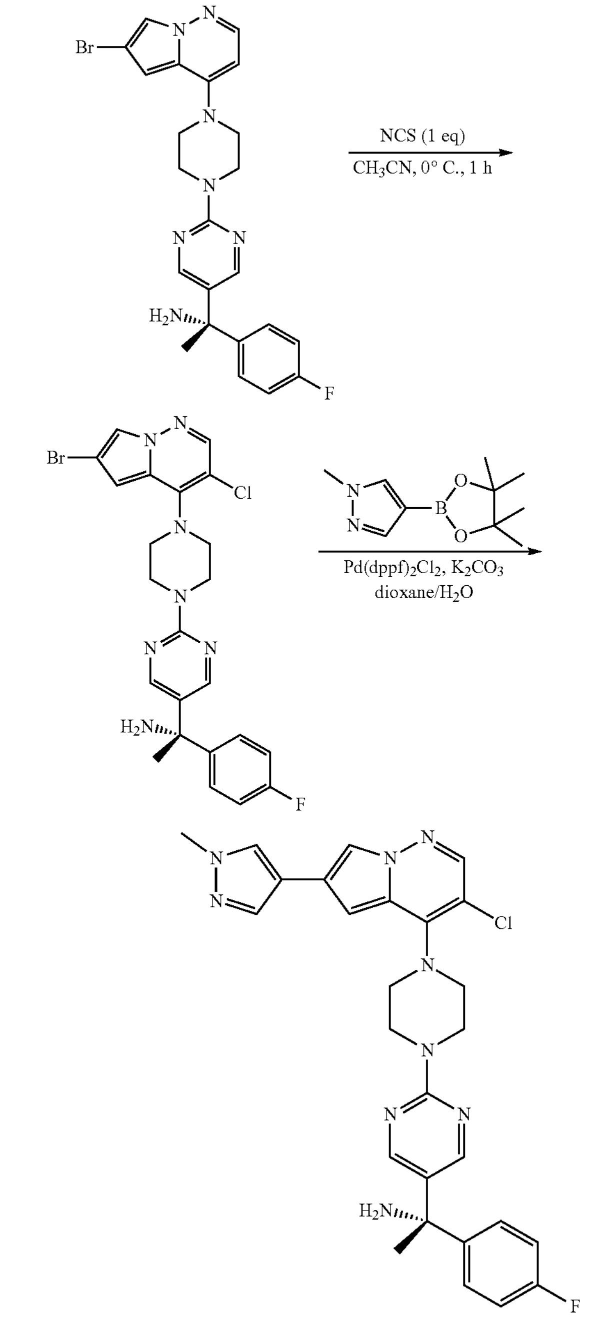

Step 1: Synthesis of (S)-1-(2-(4-(6-bromopyrrolo[1,2-b]pyridazin-4-yl)piperazin-1-yl)pyrimidin-5-yl)-1-(4-fluorophenyl)ethanamine

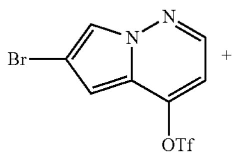

-continued

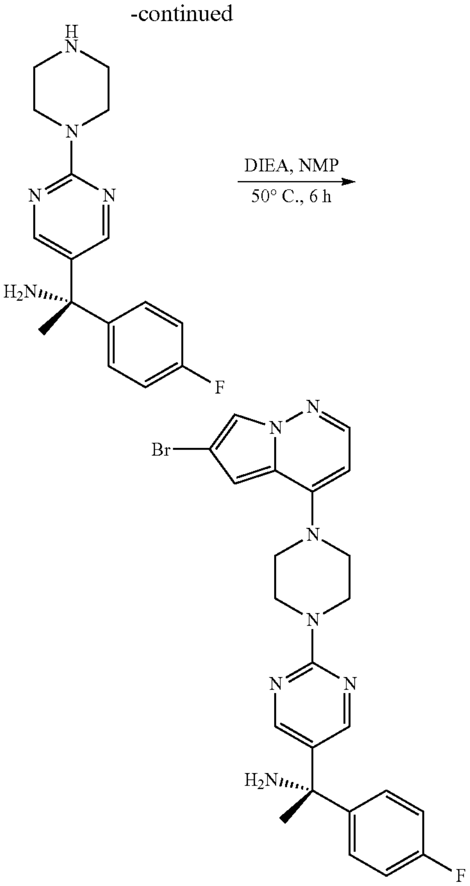

A mixture of 6-bromopyrrolo[1,2-b]pyridazin-4-yl trifluoromethanesulfonate (518 mg, 1.5 mmol), (S)-1-(4-fluorophenyl)-1-(2-(piperazin-1-yl)pyrimidin-5-yl)ethanamine (452 mg, 1.5 mmol) and DIEA (388 mg, 3 mmol) in NMP (10 mL) was stirred at 50° C. for 6 hours. The reaction was cooled to room temperature and then washed with water. The organic layer was dried and concentrated. The residue was purified by silica gel column (PE/EtOAc=1:1) to give the title product (355 mg) as a yellow solid. MS (ES+) $C_{23}H_{23}BrFN_7$ requires: 495, 497, found: 496, 498 $[M+H]^+$.

Step 2: Synthesis of (S)-1-(2-(4-(6-bromo-3-chloropyrrolo[1,2-b]pyridazin-4-yl)piperazin-1-yl)pyrimidin-5-yl)-1-(4-fluorophenyl)ethanamine

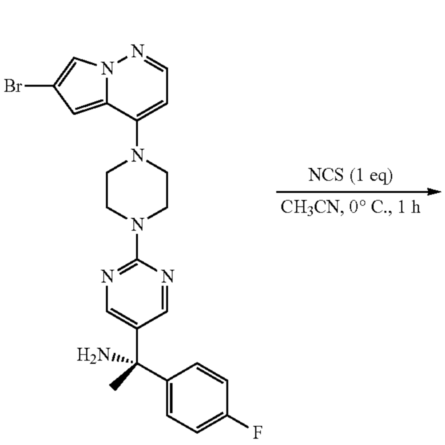

-continued

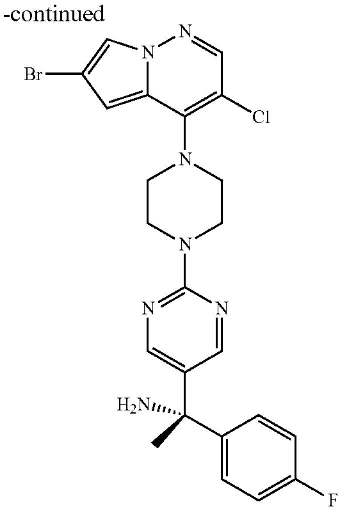

To a solution of (S)-1-(2-(4-(6-bromopyrrolo[1,2-b]pyridazin-4-yl)piperazin-1-yl)pyrimidin-5-yl)-1-(4-fluorophenyl)ethanamine (200 mg, 0.4 mmol) in acetonitrile (5 mL) was added NCS (54 mg, 0.4 mmol) at room temperature. The mixture was stirred at room temperature for 1 hour. The reaction mixture was concentrated and purified by silica gel column (PE/EtOAc=1:1) to give the title product (32 mg) as a yellow solid. MS (ES+) $C_{23}H_{22}BrClFN_7$ requires: 529, 531, found: 530, 532 $[M+H]^+$.

Step 3: Synthesis of (S)-1-(2-(4-(3-chloro-6-(1-methyl-1H-pyrazol-4-yl)pyrrolo[1,2-b]pyridazin-4-yl)piperazin-1-yl)pyrimidin-5-yl)-1-(4-fluorophenyl) ethanamine

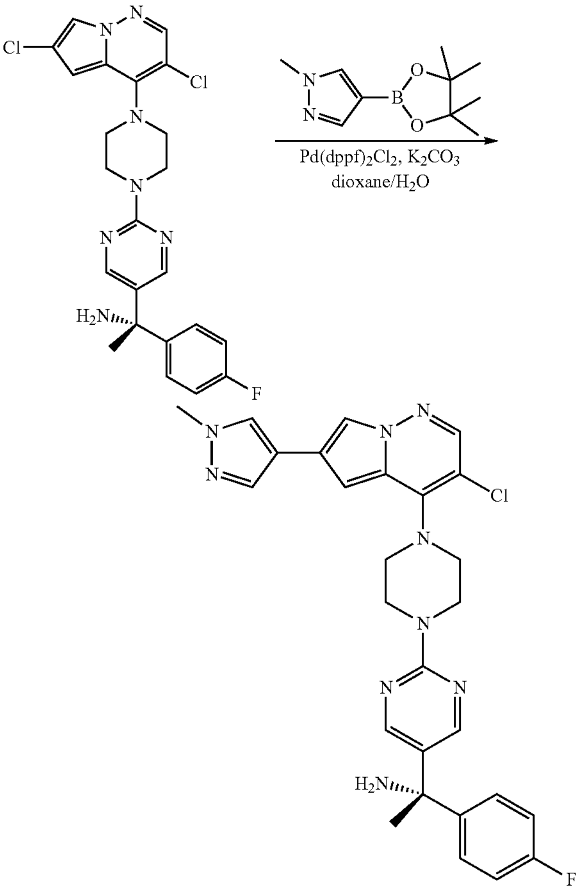

A mixture of (S)-1-(2-(4-(6-bromo-3-chloropyrrolo[1,2-b]pyridazin-4-yl)piperazin-1-yl)pyrimidin-5-yl)-1-(4-fluorophenyl)ethanamine (32 mg, 0.06 mmol), 1-methyl-4-(4,4,5,5-tetramethyl-1,3,2-dioxaborolan-2-yl)-1H-pyrazole (19 mg, 0.09 mmol), $Pd(dppf)_2Cl_2$ (5 mg, 0.006 mmol) and $K_2CO_3$ (16 mg, 0.12 mmol) in dioxane/water (4 mL/1 mL) was purged with N2 and stirred at 100° C. for 6 hours. The reaction mixture was cooled and filtered through Celite. The filtrate was concentrated and the residue was purified by Prep-HPLC to give the title product (19 mg) as a yellow solid.

Example 4. Synthesis of (S)-4-(4-(5-(1-amino-1-(4-fluorophenyl)ethyl)pyrimidin-2-yl)piperazin-1-yl)-6-(1-methyl-1H-pyrazol-4-yl)pyrrolo[1,2-b]pyridazine-3-carbonitrile (Compound 4)

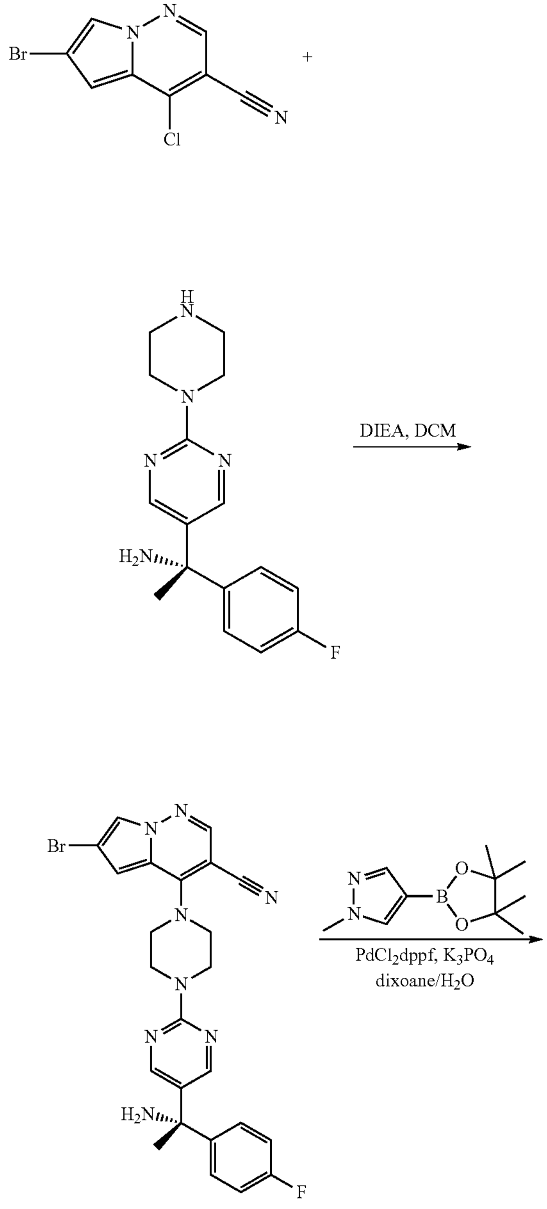

-continued

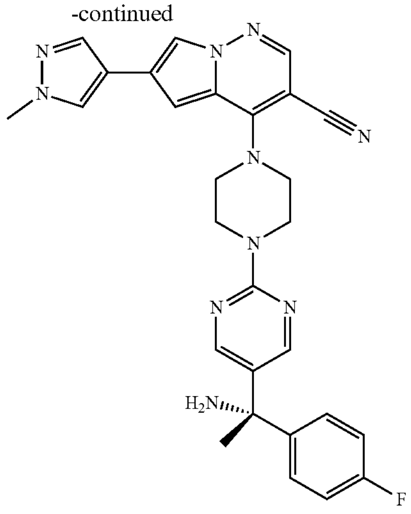

Step 1: Synthesis of (S)-4-(4-(5-(1-amino-1-(4-fluorophenyl)ethyl)pyrimidin-2-yl)piperazin-1-yl)-6-bromopyrrolo[1,2-b]pyridazine-3-carbonitrile

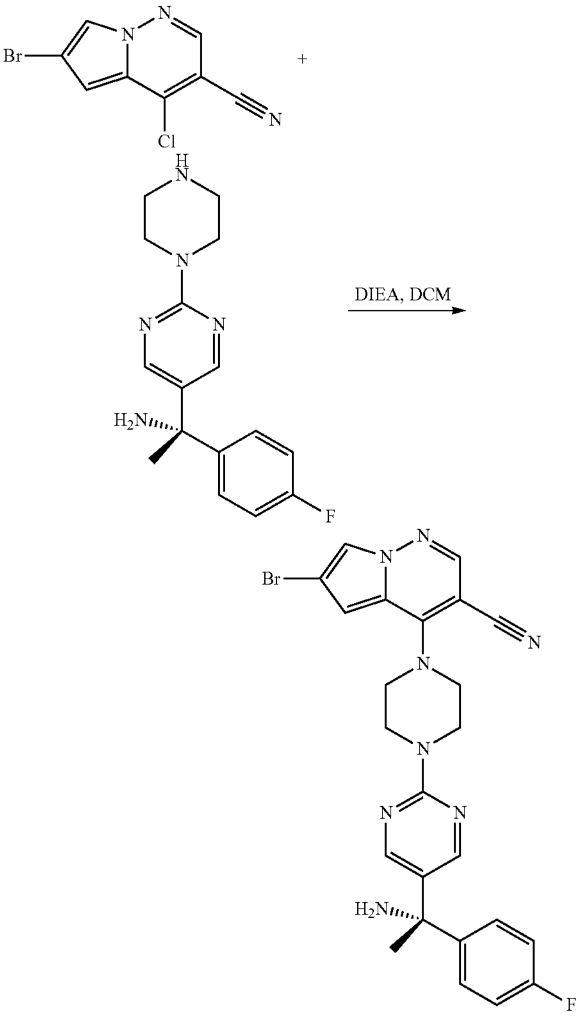

To a solution of 6-bromo-4-chloropyrrolo[1,2-b]pyridazine-3-carbonitrile (WO2012125886, 80 mg, 0.31 mmol) in DCM (10 mL) was added (S)-1-(4-fluorophenyl)-1-(2-(piperazin-1-yl)pyrimidin-5-yl)ethanamine (110 mg, 0.36 mmol) and DIPEA (80 mg, 0.62 mmol). The mixture was stirred at RT for overnight. LCMS indicated complete conversion. The reaction mixture was diluted with DCM (20 mL), washed with water and brine, and dried over $Na_2SO_4$. After concentration, the title crude product was used into the next step without further purification. MS (ES+) $C_{24}H_{22}BrFN_8$ requires: 520, 522, found: 521, 523 [M+H]+.

Step 2: Synthesis of (S)-4-(4-(5-(1-amino-1-(4-fluorophenyl)ethyl)pyrimidin-2-yl)piperazin-1-yl)-6-(1-methyl-1H-pyrazol-4-yl)pyrrolo[1,2-b]pyridazine-3-carbonitrile

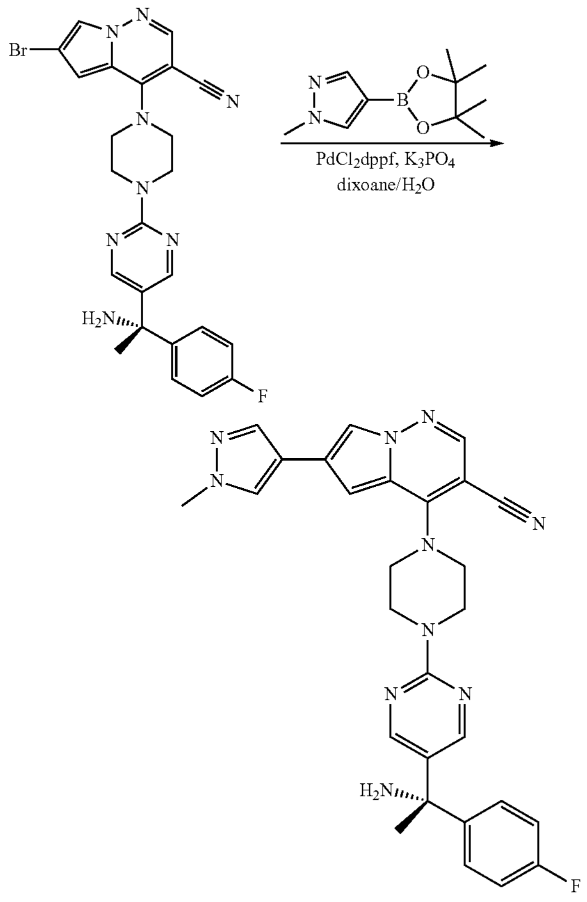

A mixture of (S)-4-(4-(5-(1-amino-1-(4-fluorophenyl)ethyl)pyrimidin-2-yl)piperazin-1-yl)-6-bromopyrrolo[1,2-b]pyridazine-3-carbonitrile (100 mg, 0.19 mmol), 1-methyl-4-(4,4,5,5-tetramethyl-1,3,2-dioxaborolan-2-yl)-1H-pyrazole (50 mg, 0.23 mmol), Pd(dppf)$_2$Cl$_2$ (30 mg, 0.04 mmol) and K$_3$PO$_4$ (120 mg, 0.57 mmol) in 1,4-dioxane and water (10 mL:1 mL) was degassed three times and purged with N2, and then heated to 100° C. for overnight under N$_2$. LCMS indicated complete conversion. The reaction mixture was cooled to RT and concentrated. The residue was directly purified by silica gel chromatography (DCM:MeOH=50:1) to give the title product (52.2 mg, yield 52%) as a light yellow solid.

The synthetic protocol that can be used to prepare the compounds disclosed herein and characterization data are indicated below. Specifically, NMR and LCMS data obtained for compounds disclosed herein are shown below.

| Compound Number | Synthetic Protocol | $^1$H NMR | MS (M + 1) |
|---|---|---|---|
| 1 | 1 | $^1$H-NMR (400 MHz, DMSO-d$_6$) δ ppm 8.4 (s, 2H), 8.03 (s, 1H), 7.91 (d, 1H, J = 1.6 Hz), 7.85 (d, 1H, J = 5.2 Hz), 7.80 (s, 1H), 7.48-7.44 (m, 2H), 7.13-7.10 (t, 2H), 6.83(d, 1H, J = 1.6 Hz), 5.98 (d, 1H, J = 5.2 Hz), 3.94-3.90 (m, 4H), 3.84 (s, 3H), 3.52-3.49 (m, 2H), 1.73 (s, 3H). | 498 |
| 2 | 1 | $^1$H-NMR (400 MHz, 6d-DMSO) δ ppm 8.41 (s, 2H), 8.12 (d, 1H, J = 5.6 Hz), 8.05 (s, 1H), 7.93 (s, 1H), 7.81 (s, 1H), 7.49-7.45 (m, 2H), 7.11 (t, 2H, J = 8.8 Hz), 6.8 (s, 1H), 3.91-3.88 (m, 4H), 3.85 (s, 3H), 3.58-3.54 (m, 4H), 1.74 (s, 3H). | 516 |
| 3 | 1 | $^1$H-NMR (400 MHz, CDCl$_3$) δ ppm 8.38 (s, 2H), 7.81 (s, 1H), 7.21 (d, 1H, J = 3.2 Hz), 7.69 (s, 1H),7.65 (s, 1H), 7.42-7.38 (m, 2H), 7.03 (t, 2H, J = 8.8 Hz), 6.82 (d, 1H, J = 1.6 Hz), 4.03-4.018 (m, 4H), 3.94 (s, 3H), 3.65-3.62 (m, 4H), 1.87 (s, 3H). | 532 |
| 4 | 1 | $^1$H-NMR (400 MHz, DMSO-d6) δ ppm 8.41 (s, 2H), 8.13 (d, 1H, J = 1.2 Hz), 8.08 (s, 1H), 8.03 (s, 1H), 7.85 (s, 1H), 7.48-7.44 (m, 2H), 7.18 (d, 1H, J = 1.2 Hz), 7.12-7.06 (m, 2H), 3.94 (hr. s., 8H), 3.84 (s, 3H), 1.73 (s, 3H). | 523 |

Biochemical Activity of Compounds

KIT, KIT mutant, and PDGFRα mutant kinase profiling was performed with recombinant enzymes including wild-type KIT, KIT V560G, KIT V559D/T670I, V559D/V654A, and PDGFRα D842V. Kinase/substrate pairs were prepared in reaction buffer (20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO). Compounds were dissolved at 10 mM in 100% DMSO, serial diluted and added to the kinase/substrate mix in final concentrations from 10 uM to 0.5 pM. Compounds were incubated with the recombinant enzymes and substrates at room temperature for 20 minutes with their respective Km for ATP. $^{33}$P-ATP (10 mCi/mL) was added to initiate the reaction. Incubation for two hours at room temperature was followed by spotting onto P81 ion exchange paper and detection of kinase activity by a filter-binding method.

Conditions for Specific Enzyme Assays:

| Enzyme | Substrate | ATP (Km) |
|---|---|---|
| c-KIT WT | poly[Glu:Tyr] (4:1) | 100 uM |
| c-KIT V560G | poly[Glu:Tyr] (4:1) | 20 uM |
| c-KIT V559D/T670I | poly[Glu:Tyr] (4:1) | 5 uM |
| c-KIT V559D/V654A | poly[Glu:Tyr] (4:1) | 20 uM |
| PDGFRα D842V | poly[Glu:Tyr] (4:1) | 1 uM |

Data was normalized to 0% and 100% inhibition controls and the IC50 calculated using a 4-parameter curve fit.

In Table 2 below, for wild-type KIT, KIT V560G, KIT V559D/T670I, V559D/V654A and PDGFRα D842V inhibitory activity, the following designations are used: <1.00 nM=A; 1.01-10.0 nM=B; 10.01-100.0 nM=C; >100 nM=D; and ND=not determined.

| Compound Number | INH-KITWT IC50 (nM) | INH-KITV560G (exon 11) IC50 (nM) | INH-KITV559D/T670I (exon 13) IC50 (nM) | INH-KITV559D/V654A (exon 13) IC50 (nM) | INH-PDGFRα D842V (exon 18) IC50 (nM) |
|---|---|---|---|---|---|
| 1 | D | B | B | B | A |
| 2 | D | C | B | C | A |
| 3 | D | C | B | D | A |
| 4 | D | B | B | C | A |

All publications and patents mentioned herein are hereby incorporated by reference in their entirety as if each individual publication or patent was specifically and individually indicated to be incorporated by reference.

Those skilled in the art will recognize, or be able to ascertain using no more than routine experimentation, many equivalents to the specific embodiments of the disclosure described herein. Such equivalents are intended to be encompassed by the following claims.

We claim:

1. A compound selected from the group consisting of:

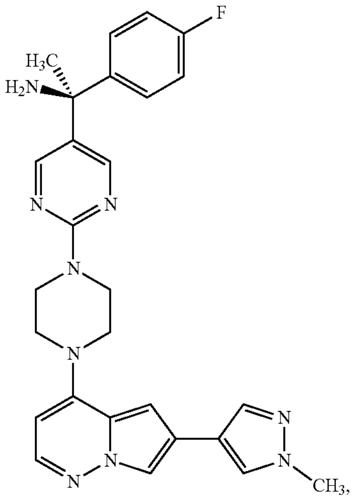

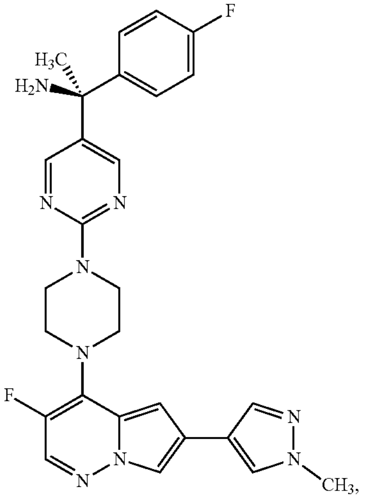

-continued

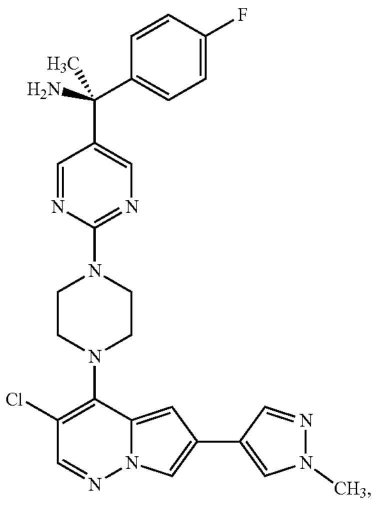

and

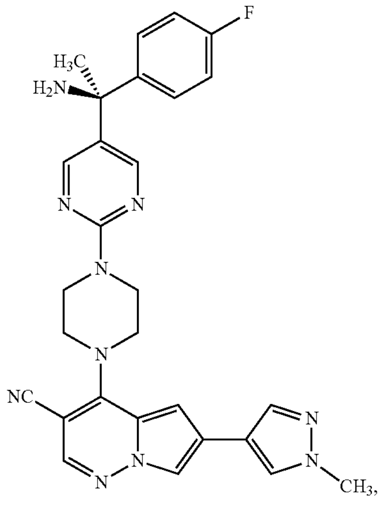 [SMILES: Cn1cc(-c2cc3c(N4CCN(c5ncc([C@@](C)(N)c6ccc(F)cc6)cn5)CC4)c(C#N)cnn3c2)cn1]

or a pharmaceutically acceptable salt thereof.

2. The compound of claim 1, wherein the compound is:

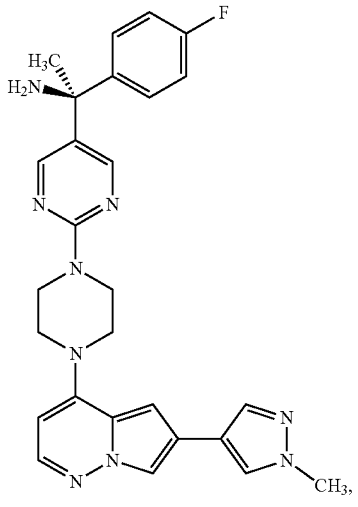 [SMILES: Cn1cc(-c2cc3c(N4CCN(c5ncc([C@@](C)(N)c6ccc(F)cc6)cn5)CC4)ccnn3c2)cn1]

or a pharmaceutically acceptable salt thereof.

3. The compound of claim 1, wherein the compound is:

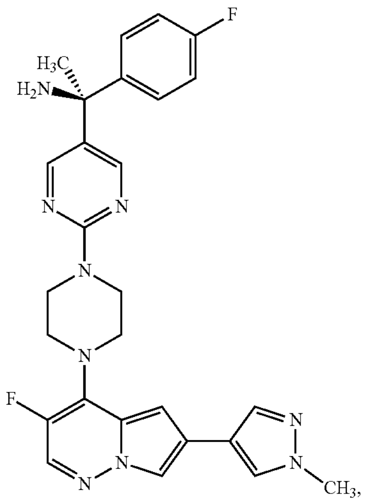 [SMILES: Cn1cc(-c2cc3c(N4CCN(c5ncc([C@@](C)(N)c6ccc(F)cc6)cn5)CC4)c(F)cnn3c2)cn1]

or a pharmaceutically acceptable salt thereof.

4. The compound of claim 1, wherein the compound is:

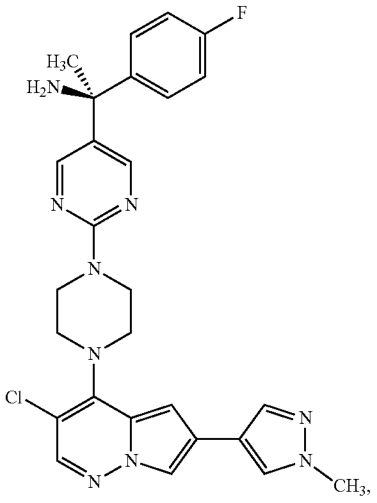 [SMILES: Cn1cc(-c2cc3c(N4CCN(c5ncc([C@@](C)(N)c6ccc(F)cc6)cn5)CC4)c(Cl)cnn3c2)cn1]

or a pharmaceutically acceptable salt thereof.

5. The compound of claim 1, wherein the compound is:

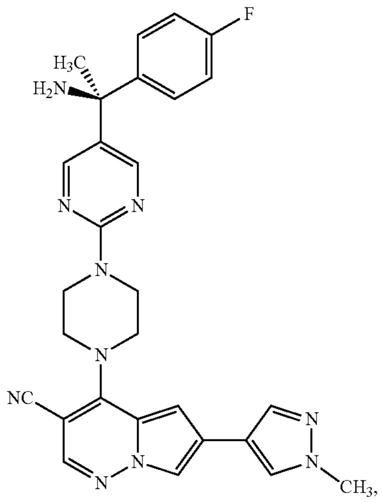 [SMILES: Cn1cc(-c2cc3c(N4CCN(c5ncc([C@@](C)(N)c6ccc(F)cc6)cn5)CC4)c(C#N)cnn3c2)cn1]

or a pharmaceutically acceptable salt thereof.

6. A pharmaceutical composition comprising a pharmaceutically acceptable carrier and at least one compound of claim 1, or a pharmaceutically acceptable salt thereof.

7. A method of treating acute myeloid leukemia in a subject in need thereof, the method comprising administering to the subject a therapeutically effective amount of at least one compound of claim 1, or a pharmaceutically acceptable salt thereof.

8. A method of treating gastrointestinal stromal tumor in a subject in need thereof, the method comprising administering to the subject a therapeutically effective amount of at least one compound of claim 1, or a pharmaceutically acceptable salt thereof.

9. A method of treating mastocytosis in a subject in need thereof, the method comprising administering to the subject a therapeutically effective amount of at least one compound of claim 1, or a pharmaceutically acceptable salt thereof.

* * * * *